US009345957B2

(12) United States Patent
Geisner et al.

(10) Patent No.: US 9,345,957 B2
(45) Date of Patent: May 24, 2016

(54) ENHANCING A SPORT USING AN AUGMENTED REALITY DISPLAY

(71) Applicant: MICROSOFT CORPORATION, Redmond, WA (US)

(72) Inventors: Kevin A. Geisner, Mercer Island, WA (US); Kathryn Stone Perez, Kirkland, WA (US); Stephen G. Latta, Seattle, WA (US); Ben J. Sugden, Woodinville, WA (US); Benjamin I. Vaught, Seattle, WA (US); Alex Aben-Athar Kipman, Redmond, WA (US); John Clavin, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 13/631,511

(22) Filed: Sep. 28, 2012

(65) Prior Publication Data

US 2013/0095924 A1    Apr. 18, 2013

Related U.S. Application Data

(63) Continuation-in-part of application No. 13/250,878, filed on Sep. 30, 2011.

(51) Int. Cl.
*G09G 5/00* (2006.01)
*A63F 13/00* (2014.01)
(Continued)

(52) U.S. Cl.
CPC ............. *A63F 13/00* (2013.01); *G02B 27/017* (2013.01); *G06F 3/012* (2013.01); *G06F 3/013* (2013.01);
(Continued)

(58) Field of Classification Search
CPC ............ G09G 5/00; G06K 9/00; A63F 13/00; A63F 9/24; A63F 13/005; A63F 13/12; A63F 13/06; A63F 13/10; G06F 3/013; G06F 3/01; G06F 3/011; G06F 3/017; G06F 3/012; G06T 19/006; G02B 27/017; G09B 19/038
USPC ............. 345/633, 634, 419, 156, 8, 103, 107; 463/32; 382/103, 107
See application file for complete search history.

(56) References Cited

U.S. PATENT DOCUMENTS 5,333,874 A    8/1994  Arnold et al.
5,401,026 A    3/1995  Eccher et al.
(Continued)

OTHER PUBLICATIONS

"GSA Advanced Golf Simulators", [retrieved on Nov. 14, 2011], Retrieved from the Internet: <URL: http://www.golf-simulators.com/Software.htm>, 12 pages.
(Continued)

*Primary Examiner* — Phi Hoang
*Assistant Examiner* — Michael Le
(74) *Attorney, Agent, or Firm* — Dan Choi; Judy Yee; Micky Minhas

(57) ABSTRACT

Technology is described for providing a personalized sport performance experience with three dimensional (3D) virtual data displayed by a near-eye, augmented reality display of a personal audiovisual (A/V) apparatus. A physical movement recommendation is determined for the user performing a sport based on skills data for the user for the sport, physical characteristics of the user, and 3D space positions for at least one or more sport objects. 3D virtual data depicting one or more visual guides for assisting the user in performing the physical movement recommendation may be displayed from a user perspective associated with a display field of view of the near-eye AR display. An avatar may also be displayed by the near-eye AR display performing a sport. The avatar may perform the sport interactively with the user or be displayed performing a prior performance of an individual represented by the avatar.

20 Claims, 17 Drawing Sheets

(51) Int. Cl.
*G06T 19/00* (2011.01)
*G06F 3/01* (2006.01)
*G02B 27/01* (2006.01)
*G09B 19/00* (2006.01)
*H04N 13/04* (2006.01)

(52) U.S. Cl.
CPC .......... *G06T 19/006* (2013.01); *G09B 19/0038* (2013.01); *A63F 2300/1093* (2013.01); *A63F 2300/204* (2013.01); *A63F 2300/301* (2013.01); *A63F 2300/6676* (2013.01); *A63F 2300/69* (2013.01); *G02B 2027/014* (2013.01); *G02B 2027/0178* (2013.01); *G02B 2027/0187* (2013.01); *H04N 13/044* (2013.01); *H04N 13/0468* (2013.01); *H04N 13/0484* (2013.01)

(56) References Cited

U.S. PATENT DOCUMENTS

| | | | |
|---|---|---|---|
| 5,728,006 A | 3/1998 | Teitell et al. | |
| 5,762,561 A | 6/1998 | Zine | |
| 5,826,578 A | 10/1998 | Curchod | |
| 5,826,874 A | 10/1998 | Teitell et al. | |
| 6,045,446 A * | 4/2000 | Ohshima | 463/2 |
| 6,217,444 B1 | 4/2001 | Kataoka et al. | |
| 6,224,387 B1 | 5/2001 | Jones | |
| 6,517,353 B1 | 2/2003 | Jones | |
| 6,567,536 B2 * | 5/2003 | McNitt et al. | 382/107 |
| 6,623,370 B1 | 9/2003 | Willer | |
| 6,663,498 B2 | 12/2003 | Stipan | |
| 6,767,282 B2 | 7/2004 | Matsuyama et al. | |
| 7,057,582 B2 | 6/2006 | Ebersole | |
| 7,693,702 B1 | 4/2010 | Kerner | |
| 7,744,482 B1 | 6/2010 | Watson | |
| 7,815,516 B1 | 10/2010 | Mortimer et al. | |
| 7,922,586 B2 | 4/2011 | Heckendorf, III et al. | |
| 8,029,359 B2 | 10/2011 | Cheng | |
| 8,432,489 B2 | 4/2013 | Arseneau | |
| 2003/0227470 A1 | 12/2003 | Genc | |
| 2005/0113649 A1 | 5/2005 | Bergantino | |
| 2005/0227791 A1 * | 10/2005 | McCreary | A63B 69/3658 473/407 |
| 2006/0038833 A1 | 2/2006 | Mallinson et al. | |
| 2006/0053377 A1 | 3/2006 | Newell | |
| 2006/0250322 A1 | 11/2006 | Hall | |
| 2006/0277474 A1 | 12/2006 | Robarts | |
| 2007/0013515 A1 | 1/2007 | Johnson | |
| 2007/0024438 A1 | 2/2007 | Chen | |
| 2008/0018667 A1 | 1/2008 | Cheng | |
| 2008/0259096 A1 | 10/2008 | Huston | |
| 2009/0111434 A1 | 4/2009 | Yu | |
| 2009/0262946 A1 | 10/2009 | Dunko | |
| 2009/0300551 A1 | 12/2009 | French et al. | |
| 2010/0035726 A1 | 2/2010 | Fisher et al. | |
| 2010/0111387 A1 | 5/2010 | Christiansen | |
| 2010/0171758 A1 | 7/2010 | Maassel | |
| 2010/0208033 A1 | 8/2010 | Edge | |
| 2010/0238161 A1 | 9/2010 | Varga | |
| 2010/0302142 A1 | 12/2010 | French et al. | |
| 2010/0315418 A1 * | 12/2010 | Woo | 345/419 |
| 2011/0065496 A1 | 3/2011 | Gagner et al. | |
| 2011/0087137 A1 | 4/2011 | Hanoun | |
| 2011/0098109 A1 * | 4/2011 | Leake et al. | 463/30 |
| 2011/0112904 A1 | 5/2011 | Stupp | |
| 2011/0137724 A1 | 6/2011 | Ramchandran | |
| 2011/0221656 A1 * | 9/2011 | Haddick et al. | 345/8 |
| 2011/0270135 A1 * | 11/2011 | Dooley et al. | 600/595 |
| 2011/0301927 A1 | 12/2011 | Ok | |
| 2011/0318717 A1 | 12/2011 | Adamowicz | |
| 2012/0005222 A1 | 1/2012 | Bhagwan et al. | |
| 2012/0062445 A1 | 3/2012 | Haddick et al. | |
| 2012/0068980 A1 | 3/2012 | Kitahara | |
| 2012/0072302 A1 | 3/2012 | Chen et al. | |
| 2012/0113223 A1 | 5/2012 | Hilliges | |
| 2012/0120499 A1 | 5/2012 | Harrison | |
| 2012/0133650 A1 | 5/2012 | Lee | |
| 2012/0212398 A1 | 8/2012 | Border et al. | |
| 2012/0233002 A1 | 9/2012 | Abujbara | |
| 2012/0253485 A1 | 10/2012 | Weast et al. | |
| 2012/0329432 A1 | 12/2012 | Gupta | |
| 2013/0065692 A1 | 3/2013 | Aronzon et al. | |
| 2013/0083003 A1 | 4/2013 | Perez | |
| 2013/0265333 A1 | 10/2013 | Ainsworth | |

OTHER PUBLICATIONS

Conroy, "How to Create Your Own Virtual Golf Course Game", [retrieved on Nov. 14, 2011], Retrieved from the Internet: <URL:http://www.ehow.com/how_5672075_create-virtual-golf-course-game.html>, 5 pages.
Office Action dated Jul. 26, 2013, U.S. Appl. No. 13/250,878, 24 pages.
Response to Office Action filed Oct. 18, 2013, U.S. Appl. No. 13/250,878, 9 pages.
Office Action dated Feb. 4, 2014, U.S. Appl. No. 13/250,878, 43 pages.
Response to Office Action filed May 2, 2014, U.S. Appl. No. 13/250,878, 10 pages.
Office Action dated May 21, 2014, U.S. Appl. No. 13/250,878, 48 pages.
Response to Office Action filed Aug. 21, 2014, U.S. Appl. No. 13/250,878, 12 pages.
Office Action dated Mar. 13, 2015, U.S. Appl. No. 13/250,878, 41 pages.
Final Office Action dated Nov. 21, 2014, U.S. Appl. No. 13/250,878, 44 pages.
Response to Office Action filed Feb. 14, 2015, U.S. Appl. No. 13/250,878, 11 pages.
Response to Office Action dated Jun. 15, 2015 in U.S. Appl. No. 13/250,878, 11 pages.
Office Action dated Sep. 9, 2015 in U.S. Appl. No. 13/250,878, 50 pages.

* cited by examiner

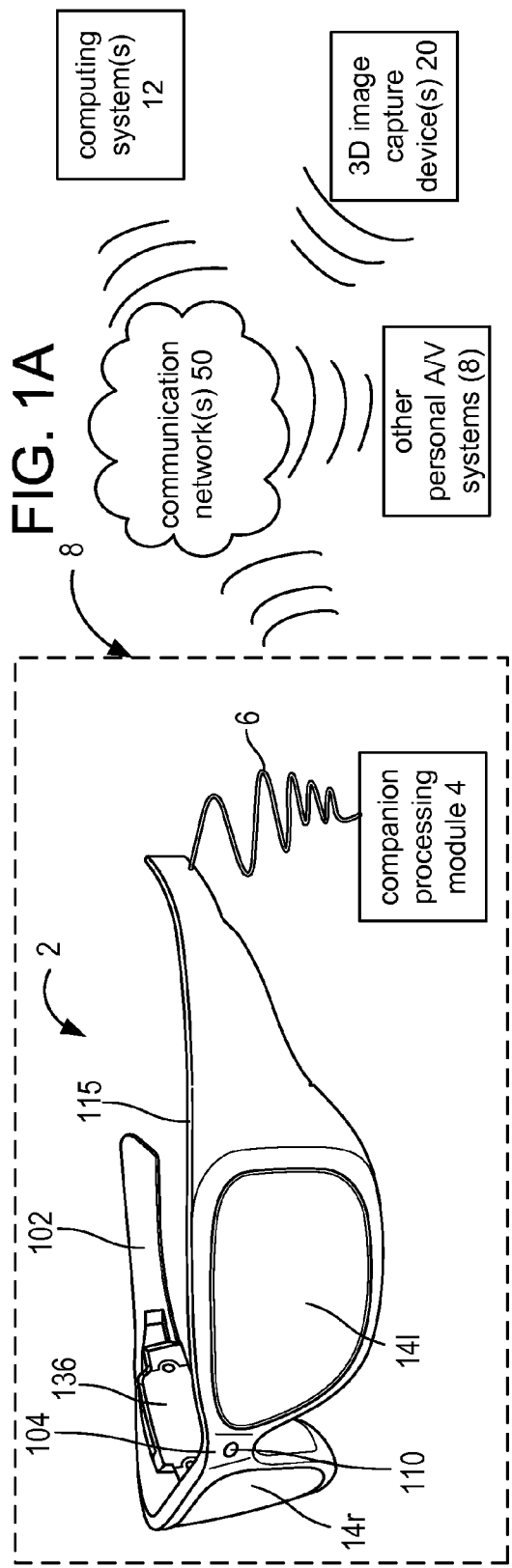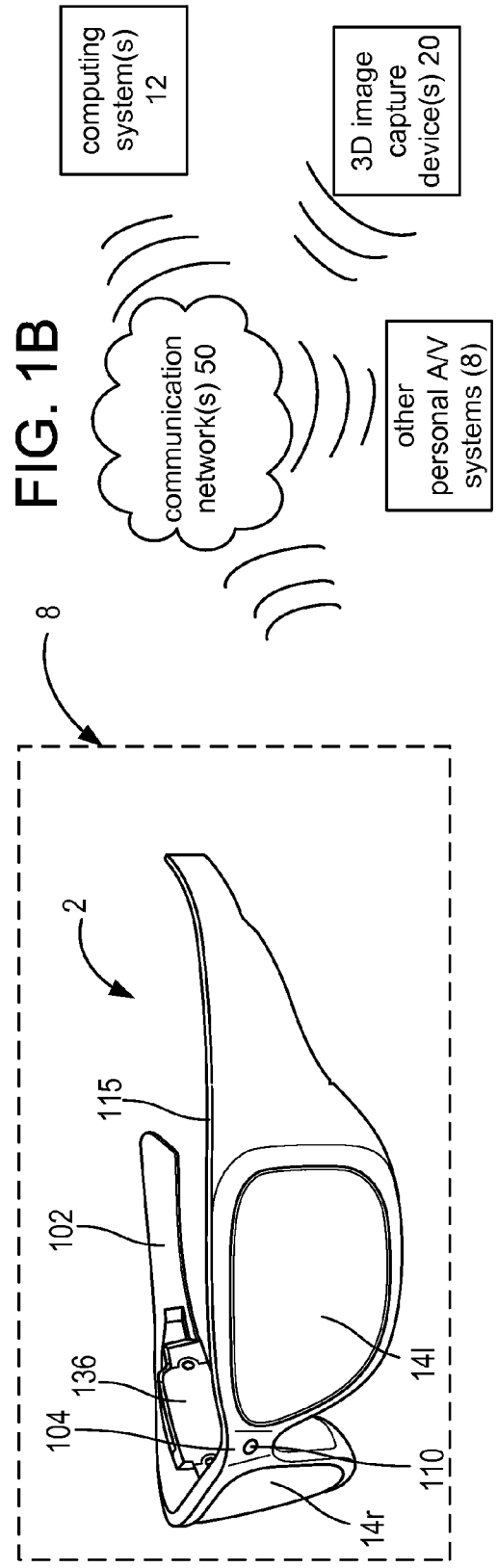

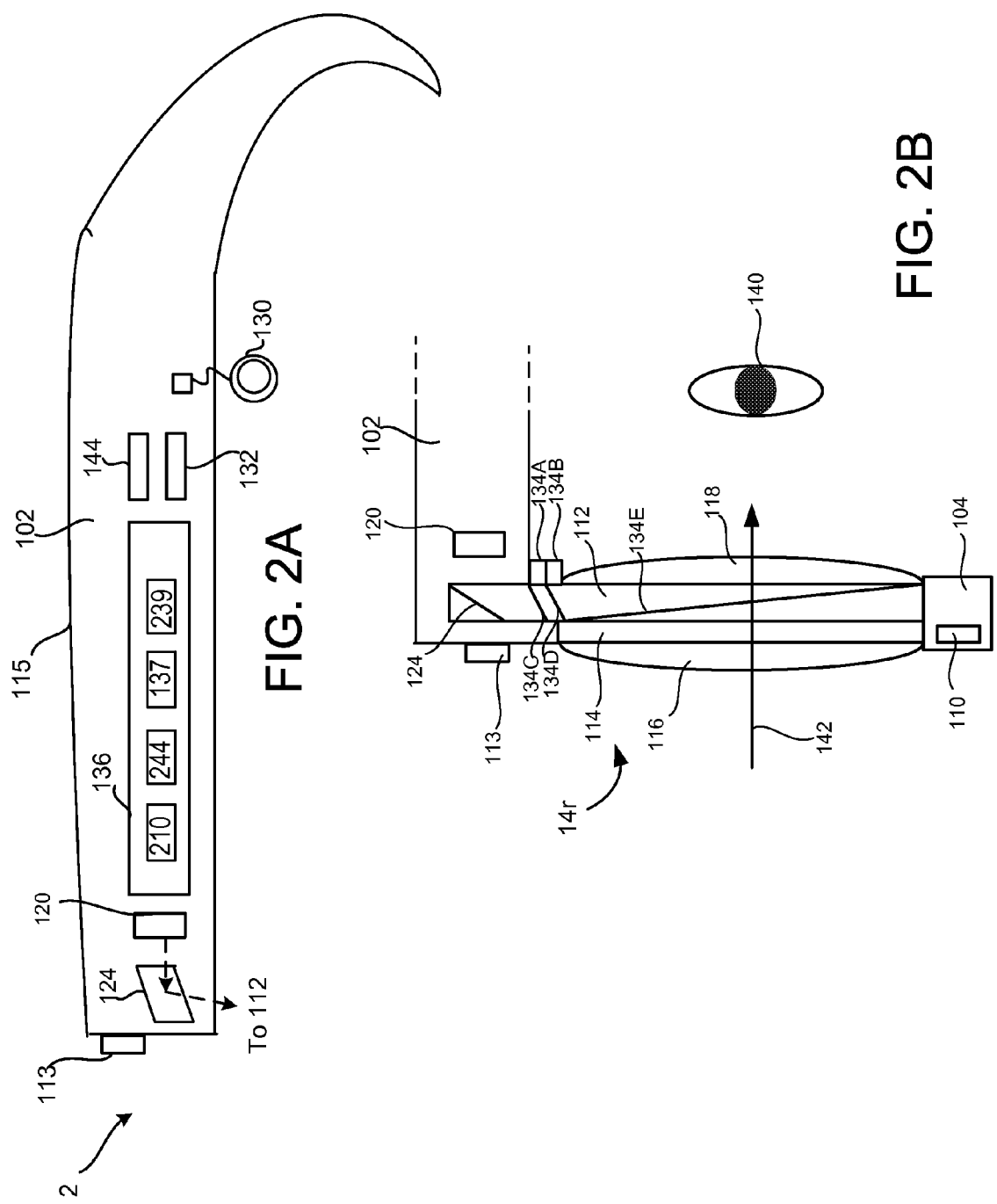

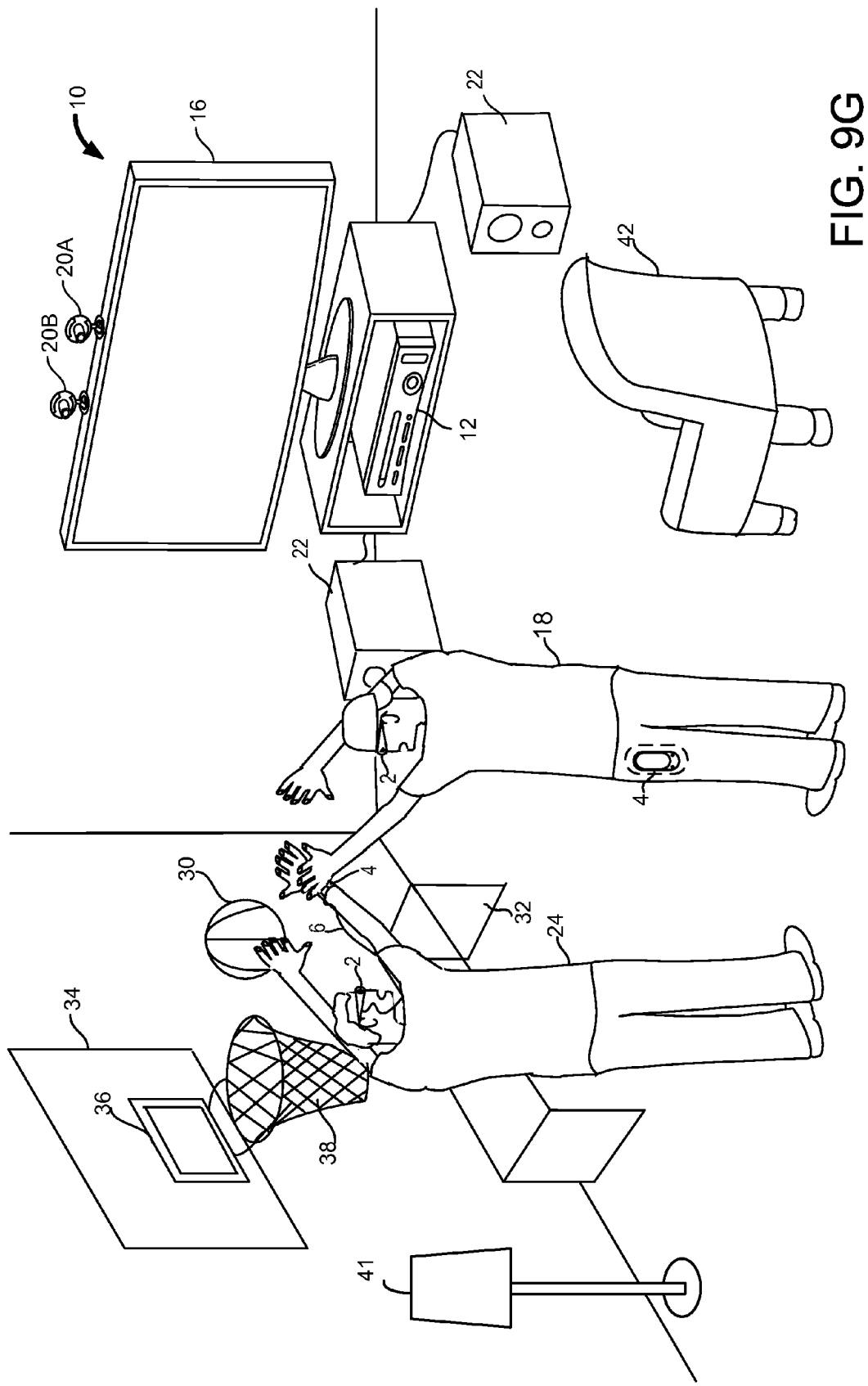

ENHANCING A SPORT USING AN AUGMENTED REALITY DISPLAY

CROSS-REFERENCE TO RELATED APPLICATIONS

This is a continuation-in-part application of U.S. patent application Ser. No. 13/250,878, titled "Personal Audio/Visual System," to K. Stone-Perez et al., filed Sep. 30, 2011, published as US 2013/0083003 on Apr. 4, 2013, and incorporated herein by reference.

BACKGROUND

When playing a sport, a person may daydream as if he is playing with his favorite sports star. At other times, he or she may wish an instructor could be where he or she is playing and providing advice for improving his or her performance in real time and under current environmental conditions for play. Additionally, even when a coach or friend is with the player and giving advice, the player may not be able to translate what was heard or seen into his or her own physical actions.

SUMMARY

Technology is described for providing a personalized sport performance experience with three dimensional (3D) virtual data being displayed by a near-eye, augmented reality (AR) display of a personal audiovisual (A/V) apparatus. A visual guide for tracking a sport object like a ball or providing a tip on performing a sport movement may be displayed from the user perspective in some examples. In other embodiments, a user can interactively play a sport with an avatar which may represent another person like a friend or celebrity, or even the user. In other embodiments, an avatar performing a prior performance may be displayed by the AR display from a user perspective associated with a display field of view of the display. As these examples illustrate, coaching, gaging one's performance, and play may be enhanced by the various embodiments of the technology.

The technology provides one or more embodiments of a method for providing a personalized sport performance experience with three dimensional (3D) virtual data being displayed by a near-eye, augmented reality (AR) display of a personal audiovisual (A/V) apparatus. An embodiment of the method comprises automatically identifying a physical location which the personal A/V apparatus is within based on location data detected by the personal A/V apparatus and automatically identifying at least one or more sports objects in a sport performance area associated with the physical location based on a three dimensional mapping of objects in the physical location.

Physical characteristics of a user and skills data for a sport stored for the user in user profile data are accessed from a memory. A physical movement recommendation is determined by a processor for the user performing the sport based on the skills data for the sport, the physical characteristics of the user, and 3D space positions for the at least one or more sport objects in the physical location. Three dimensional (3D) virtual data depicting one or more visual guides for assisting the user in performing the physical movement recommendation is displayed from a user perspective associated with a display field of view of the near-eye AR display.

The technology provides one or more embodiments of a portable personal audiovisual (A/V) apparatus for providing a personalized sport performance experience with three dimensional (3D) virtual data. An embodiment of the portable personal A/V apparatus comprises a near-eye, augmented reality (AR) display having a display field of view and being supported by a near-eye support structure. One or more processors have access to memory storing physical characteristics of a user wearing the personal A/V apparatus and skills data for the user for one or more sports. A natural user interface of the apparatus includes at least one image capture device communicatively coupled to the one or more processors and being supported by the near-eye support structure for tracking a physical sport movement being performed by a user.

The one or more processors determine a physical sport movement recommendation based on a sport being played, skills data for the user for the sport being played, and one or more objects in a sport performance area in which the user is playing the sport. The one or more processors control the near-eye, AR display of the personal A/V apparatus for displaying 3D virtual data for assisting the user in performing the physical sport movement recommendation from a user perspective associated with the display field of view.

The technology provides one or more embodiments of one or more processor readable storage devices comprising instructions encoded thereon which instructions cause one or more processors to execute a method for providing a personalized sport performance experience with three dimensional (3D) virtual data displayed by a near-eye, augmented reality (AR) display of a personal audiovisual (A/V) apparatus. An embodiment of the method comprises receiving data indicating user selection of an avatar for display performing a sport during a sport performance session. One or more memories storing sport performance data for the avatar are accessed by a processor of the personal A/V apparatus. 3D virtual data of the avatar performing the sport in a context of the sport performance session is displayed based on the sport performance data for the avatar from a user perspective associated with a display field of view of the near-eye, AR display of the personal A/V apparatus.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 1A is a block diagram depicting example components of an embodiment of a portable, personal audiovisual (A/V) apparatus having a near-eye, augmented reality display.

FIG. 1B is a block diagram depicting example components of another embodiment of a portable, personal audiovisual (A/V) apparatus having a near-eye, augmented reality display.

FIG. 2A is a side view of an eyeglass temple of a frame in an embodiment of the personal audiovisual (A/V) apparatus having an optical see-through, AR display embodied as eyeglasses providing support for hardware and software components.

FIG. 2B is a top view of an embodiment of a display optical system of a near-eye, optical see-through, augmented reality display.

FIG. 9G illustrates an example of displaying virtual data of an avatar interacting with a user during a sport performance session.

DETAILED DESCRIPTION

Figure 3:
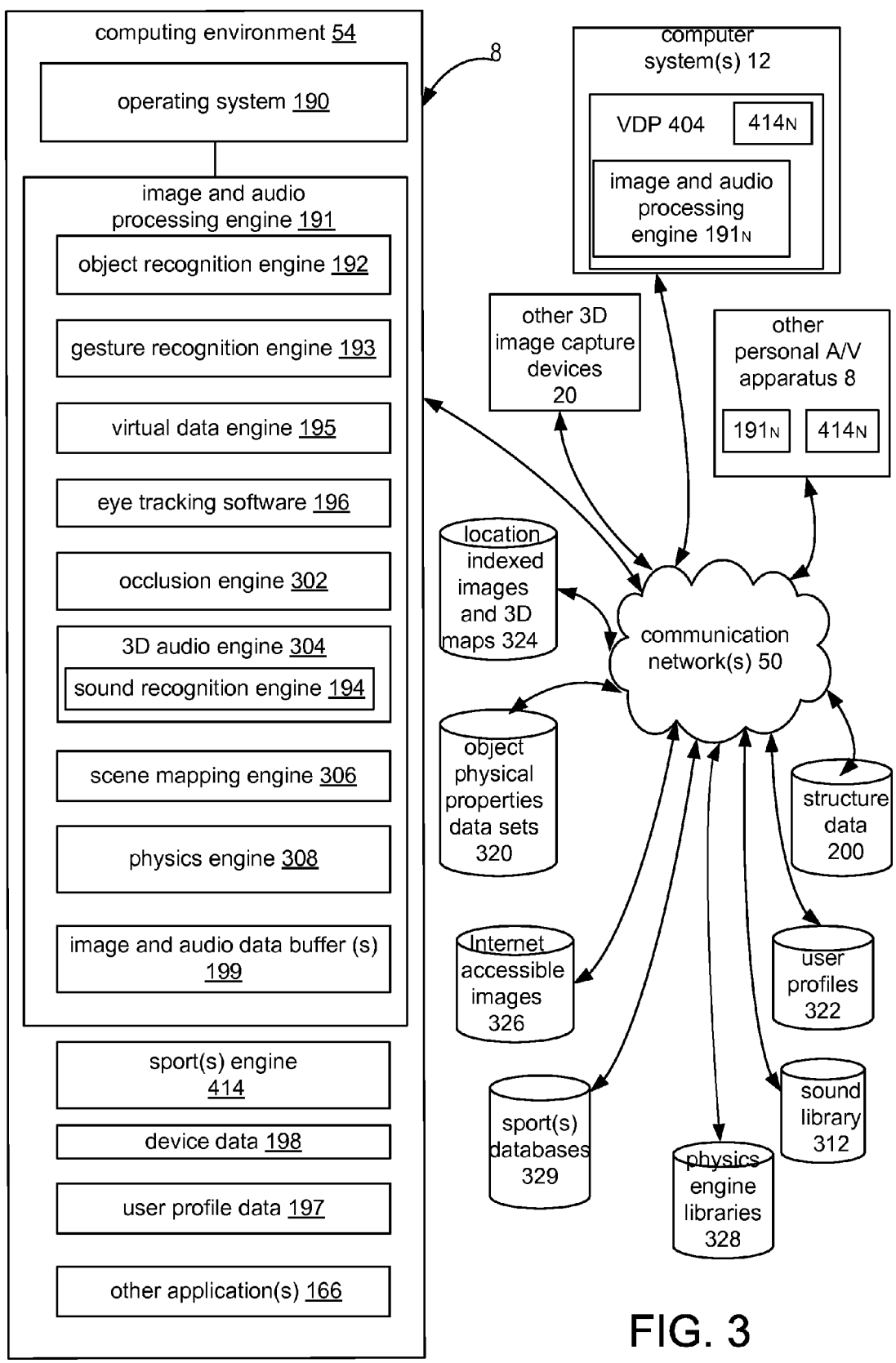
FIG. 3 is a block diagram of a system from a software perspective for providing a personalized sport performance experience with three dimensional (3D) virtual data being displayed by a near-eye, AR display of a portable, personal audiovisual (A/V) apparatus.

A personal A/V apparatus including a near-eye, augmented reality (AR) display can enhance performing a sport by displaying virtual data. Some examples of sports are running, golf, basketball, baseball, swimming, etc. A user of the personal A/V apparatus may be playing with real sport equipment or virtual sport equipment displayed by the AR display. Furthermore, a user may be performing a sport at a real sport performance location like a real golf course, a real golf range, a real basketball court, or a real physical location like a neighborhood for a run. A user may also be performing a sport in the context of a virtual sport performance area which may be displayed by the personal A/V apparatus or by the apparatus and other display devices. Avatars for presenting a performance or for interaction with the user may be displayed as well. In some embodiments, a sport engine provides a physical sport movement recommendation for a user based on a current context in a sport performance session and user skills data. Some examples of information a physical sport movement recommendation may include are what piece of sports equipment to use, a direction of aim, a suggested body movement (e.g. duck, run), a position on a field or court at which to perform the movement, and a strength to use for a movement. A user's physical sport movement may also be tracked and analyzed for updating skills data for the user.

A user using a near-eye, AR display sees virtual objects displayed with real objects in real time. In particular, a user wearing an optical see-through, augmented reality display device actually sees with his or her natural sight a real object, which is not occluded by image data of a virtual object or virtual effects, in a display field of view of the see-through display, hence the names see-through display and optical see-through display. For other types of augmented reality displays like video-see displays, sometimes referred to as video see-through displays, or a display operating in a video-see mode, the display is not really see-through because the user does not see real objects with his natural sight, but sees displayed image data of unoccluded real objects as they would appear with natural sight as well as image data of virtual objects and virtual effects. References to a see-through display below are referring to an optical see-through display.

Image data may be moving image data like video as well as still image data. Image data may also be three dimensional. An example of 3D image data is a hologram. Image data may be that captured, and in some examples displayed, of real objects, or image data may be generated to illustrate virtual objects or imagery. Virtual image data, referred to hereafter as virtual data, is image data of a virtual object or virtual effect. An example of a virtual effect is an environmental condition like fog or rain. Another example of a virtual effect may be a simulated effect on a real object, like a smashing of a window when the real is still intact, or a displayed change of color of one's shirt. Virtual data which is registered to an object, real or virtual, means the data tracks its position in the display field of view in reference to or dependent upon a position of the object to which it is registered.

Virtual data is seen through a near-eye, augmented reality (AR) display of the personal A/V system from a user perspective which is not predefined as the display moves with user movements. The display field of view approximates a user field of view as seen from a user perspective (where a user is looking from). A user perspective may be associated with a display field of view. A user perspective may be approximated with varying degrees of accuracy. For example, a predetermined approximation of a user perspective may be associated with a near-eye AR display without reference to specific user data. In other examples, more sophisticated techniques may use individual gaze determined from eye tracking data to more precisely pinpoint from where a user is looking. In some embodiments, a user perspective of an object, real or virtual, is determined from a position and orientation of the object in the display field of view.

In some embodiments, the display field of view, may be mapped by a view dependent coordinate system, having orthogonal X, Y and Z axes in which a Z-axis represents a depth position from a reference point on the personal A/V apparatus.

FIG. 1A is a block diagram depicting example components of an embodiment of a personal audiovisual (A/V) apparatus 8. Portable personal A/V apparatus 8 includes an optical see-through, augmented reality display device as a near-eye, augmented reality display device 2 in communication with a companion processing module 4 via a wire 6 in this example or wirelessly in other examples. In this embodiment, head mounted display device 2 is in the shape of eyeglasses in a frame 115, with a display optical system 14, 14r and 14l, for each eye in which image data is projected into a user's eye to generate a display of the image data while a user also sees through the display optical systems 14 for an actual direct view of the real world.

The use of the term "actual direct view" refers to the ability to see real world objects directly with the human eye, rather than seeing created image representations of the objects. For example, looking through glass at a room allows a user to have an actual direct view of the room, while viewing a video of a room on a television is not an actual direct view of the room. Each display optical system 14 is also referred to as a see-through display, and the two display optical systems 14 together may also be referred to as a see-through, meaning optical see-through, augmented reality display 14.

Frame 115 provides a support structure for holding elements of the apparatus in place as well as a conduit for electrical connections. In this embodiment, frame 115 provides a convenient eyeglass frame as support for the elements of the apparatus discussed further below. Some other example of a near-eye support structure are a visor frame or a goggles support. The frame 115 includes a nose bridge 104 with a microphone 110 for recording sounds and transmitting audio data to control circuitry 136. A side arm or temple 102 of the frame rests on each of a user's ears, and in this example the temple 102 is illustrated as including control circuitry 136 for the display device 2.

As illustrated in FIGS. 2A and 2B, an image generation unit 120 is included on each temple 102 in this embodiment as well. Also, not shown in this view, but illustrated in FIGS. 2A and 2B are outward facing capture devices 113, e.g. cameras, for recording digital image data such as still images, videos or both, and transmitting the visual recordings to the control circuitry 136 which may in turn send the captured image data to the companion processing module 4 which may also send the data to one or more computer systems 12 or to another personal A/V apparatus over one or more communication networks 50.

Figure 11:
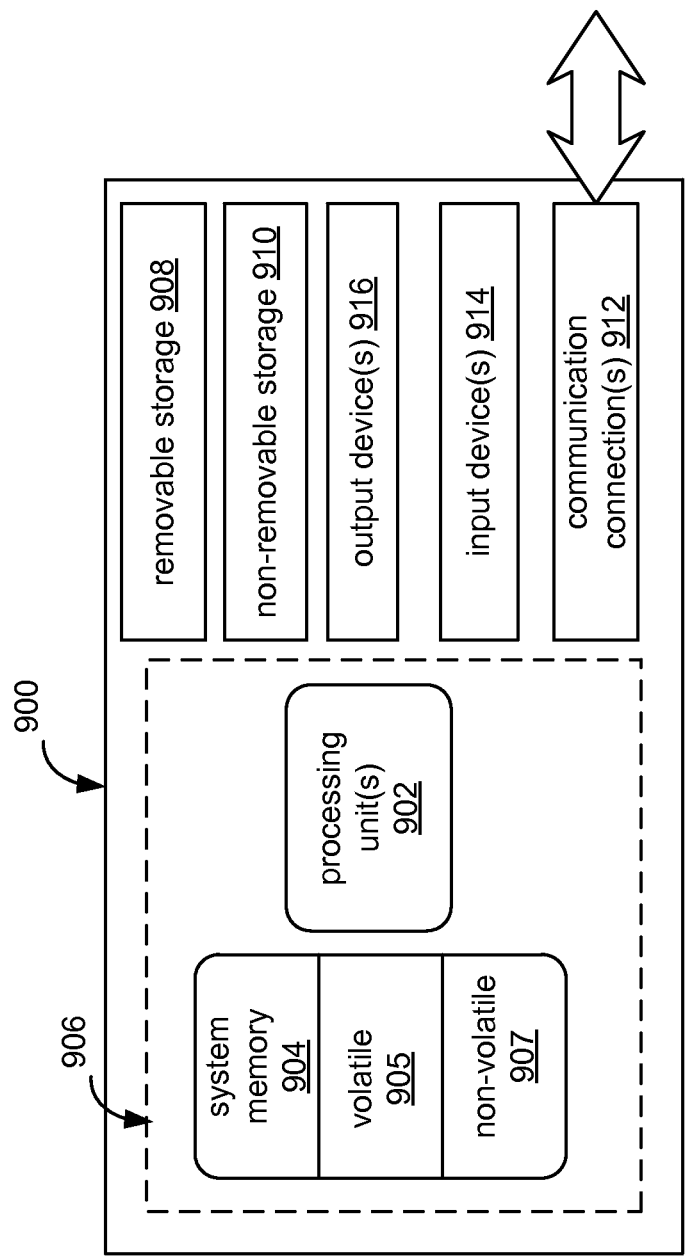
FIG. 11 is a block diagram of one embodiment of a computing system that can be used to implement a network accessible computing system or a companion processing module.

The companion processing module 4 may take various embodiments. In some embodiments, companion processing module 4 is a separate unit which may be worn on the user's body, e.g. a wrist, or be a separate device like a mobile device (e.g. smartphone). The companion processing module 4 may communicate wired or wirelessly (e.g., WiFi, Bluetooth, infrared, an infrared personal area network, RFID transmission, wireless Universal Serial Bus (WUSB), cellular, 3G, 4G or other wireless communication means) over one or more communication networks 50 to one or more computer systems 12 whether located nearby or at a remote location, other personal A/V apparatus 8 in a location or environment, for example as part of peer-to-peer communication, and if available, one or more 3D image capture devices 20 in the environment. In other embodiments, the functionality of the companion processing module 4 may be integrated in software and hardware components of the display device 2 as in FIG. 1B. Some examples of hardware components of the companion processing module 4 are shown in FIG. 11.

One or more network accessible computer system(s) 12 may be leveraged for processing power and remote data access. An example of hardware components of a computer system 12 is shown in FIG. 11. The scale and number of components may vary considerably for different embodiments of the computer system 12 and the companion processing module 4. An application may be executing on a computer system 12 which interacts with or performs processing for an application executing on one or more processors in the personal A/V apparatus 8. For example, a 3D mapping application may be executing on the one or more computers systems 12 and the user's personal A/V apparatus 8. In some embodiments, the application instances may perform in a master and client role in which a client copy is executing on the personal A/V apparatus 8 and performs 3D mapping of its display field of view, receives updates of the 3D mapping from the computer system(s) 12 including updates of objects in its view from the master 3D mapping application and sends image data, and depth and object identification data, if available, back to the master copy. Additionally, in some embodiments, the 3D mapping application executing on different personal A/V apparatus 8 in the same environment share data updates in real time, for example real object identifications in a peer-to-peer configuration between apparatus 8.

In the illustrated embodiments of FIGS. 1A and 1B, the one or more computer system 12 and the portable personal A/V apparatus 8 also have network access to one or more 3D image capture devices 20 which may be, for example one or more cameras that visually monitor one or more users and the surrounding space such that gestures and movements performed by the one or more users, as well as the structure of the surrounding space including surfaces and objects, may be captured, analyzed, and tracked. Image data, and depth data if captured by the one or more 3D capture devices 20 may supplement data captured by one or more capture devices 113 of one or more personal A/V apparatus 8 in a location. The one or more capture devices 20 may be one or more depth cameras positioned in a user environment.

FIG. 1B is a block diagram depicting example components of another embodiment of a personal audiovisual (A/V) apparatus having a near-eye augmented reality display which may communicate over a communication network 50 with other devices. In this embodiment, the control circuitry 136 of the display device 2 incorporates the functionality which a companion processing module 4 provides in FIG. 1A and communicates wirelessly via a wireless transceiver (see wireless interface 137 in FIG. 2A) over a communication network 50 to one or more computer systems 12 whether located nearby or at a remote location, other personal A/V apparatus 8 in a location or environment and, if available, a 3D image capture device in the environment.

FIG. 2A is a side view of an eyeglass temple 102 of a frame in an embodiment of the personal audiovisual (A/V) apparatus having an optical see-through, augmented reality display embodied as eyeglasses providing support for hardware and software components. At the front of frame 115 is depicted one of at least two physical environment facing capture devices 113, e.g. cameras, that can capture image data like video and still images, typically in color, of the real world to map real objects in the display field of view of the see-through display, and hence, in the field of view of the user.

In some examples, the capture devices 113 may also be depth sensitive, for example, they may be depth sensitive cameras which transmit and detect infrared light from which depth data may be determined. In other examples, a separate depth sensor (not shown) on the front of the frame 115 may also capture and provide depth data to objects and other surfaces in the display field of view. The depth data and image data form a depth map of the captured field of view of the capture devices 113 which are calibrated to include the display field of view. A three dimensional (3D) mapping of the display field of view can be generated based on the depth map.

In some embodiments, the outward facing capture devices 113 provide overlapping image data from which depth information for objects in the image data may be determined based on stereopsis. Parallax and contrasting features such as color may also be used to resolve relative positions of real objects.

The capture devices 113 are also referred to as outward facing capture devices meaning facing outward from the user's head. The illustrated capture device is a front facing capture device which is calibrated with respect to a reference point of its respective display optical system 14. One example of such a reference point is an optical axis (see 142 in FIG. 2B) of its respective display optical system 14. The calibration allows the display field of view of the display optical systems 14 to be determined from the data captured by the capture devices 113.

Control circuitry 136 provide various electronics that support the other components of head mounted display device 2. In this example, the right temple 102 includes control circuitry 136 for the display device 2 which includes a processing unit 210, a memory 244 accessible to the processing unit 210 for storing processor readable instructions and data, a wireless interface 137 communicatively coupled to the processing unit 210, and a power supply 239 providing power for the components of the control circuitry 136 and the other components of the display device 2 like the cameras 113, the microphone 110 and the sensor units discussed below. The processing unit 210 may comprise one or more processors including a central processing unit (CPU) and a graphics processing unit (GPU), particularly in embodiments without a separate companion processing module 4, which contains at least one graphics processing unit (GPU).

Inside, or mounted to temple 102, are an earphone of a set of earphones 130, an inertial sensing unit 132 including one or more inertial sensors, and a location sensing unit 144 including one or more location or proximity sensors, some examples of which are a GPS transceiver, an infrared (IR) transceiver, or a radio frequency transceiver for processing RFID data. In one embodiment, inertial sensing unit 132 includes a three axis magnetometer, a three axis gyro, and a three axis accelerometer as inertial sensors. The inertial sensors are for sensing position, orientation, and sudden accelerations of head mounted display device 2. From these sensed movements, head position, and thus orientation of the display device, may also be determined which indicate changes in the user perspective and the display field of view for which virtual data is updated to track with the user perspective.

In this embodiment, each of the devices processing an analog signal in its operation include control circuitry which interfaces digitally with the digital processing unit 210 and memory 244 and which produces or converts analog signals, or both produces and converts analog signals, for its respective device. Some examples of devices which process analog signals are the location and inertial sensing units and earphones 130 as well as the microphone 110, capture devices 113 and a respective IR illumination source 134A, and a respective IR detector or camera 134B for each eye's display optical system 14l, 14r discussed below.

Mounted to or inside temple 102 is an image source or image generation unit 120 which produces visible light representing images. The image generation unit 120 can display a virtual object to appear at a designated depth location in the display field of view to provide a realistic, in-focus three dimensional display of a virtual object which can interact with one or more real objects. Some examples of embodiments of image generation units 120 which can display virtual objects at various depths are described in the following applications which are hereby incorporated by reference: "Automatic Variable Virtual Focus for Augmented Reality Displays," having U.S. patent application Ser. No. 12/941,825 and inventors Avi Bar-Zeev and John Lewis, and which was filed Nov. 8, 2010 and "Automatic Focus Improvement for Augmented Reality Displays," having U.S. patent application Ser. No. 12/949,650 and inventors Avi Bar-Zeev and John Lewis, and which was filed Nov. 18, 2010. In these examples, a focal length for an image is changed by the image generation unit 120 resulting in a change in a region of the display field of view in which the virtual data appears. In other examples, rapid display of multiple images and a composite image of the in-focus portions of the virtual images are techniques describe which may cause displayed virtual data to appear in different focal regions.

In some embodiments, the image generation unit 120 includes a microdisplay for projecting images of one or more virtual objects and coupling optics like a lens system for directing images from the microdisplay to a reflecting surface or element 124. The reflecting surface or element 124 directs the light from the image generation unit 120 into a light guide optical element 112, which directs the light representing the image into the user's eye.

FIG. 2B is a top view of an embodiment of one side of an optical see-through, near-eye, augmented reality display device including a display optical system 14. A portion of the frame 115 of the near-eye display device 2 will surround a display optical system 14 for providing support and making electrical connections. In order to show the components of the display optical system 14, in this case 14r for the right eye system, in the head mounted display device 2, a portion of the frame 115 surrounding the display optical system is not depicted.

In the illustrated embodiment, the display optical system 14 includes an opacity filter 114 for enhancing contrast of virtual data, which is behind and aligned with optional see-through lens 116 in this example, light guide optical element 112 for projecting image data from the image generation unit 120 is behind and aligned with opacity filter 114, and optional see-through lens 118 is behind and aligned with light guide optical element 112.

Light guide optical element 112 transmits light from image generation unit 120 to the eye 140 of the user wearing head mounted, display device 2. Light guide optical element 112 also allows light from in front of the head mounted, display device 2 to be received through light guide optical element 112 by eye 140, as depicted by an arrow representing an optical axis 142 of the display optical system 14r, thereby allowing the user to have an actual direct view of the space in front of head mounted, display device 2 in addition to receiving a virtual image from image generation unit 120. Thus, the walls of light guide optical element 112 are see-through.

In this embodiment, light guide optical element 112 is a planar waveguide which acts as part of the display and also integrates eye tracking. A representative reflecting element 134E represents the one or more optical elements like mirrors, gratings, and other optical elements which direct visible light representing an image from the planar waveguide towards the user eye 140. Infrared illumination and reflections, also traverse the planar waveguide for an eye tracking system 134 for tracking the position and movement of the user's eye, typically the user's pupil. Eye movements may also include blinks. The eye tracking system 134 comprises an eye tracking IR illumination source 134A (an infrared light emitting diode (LED) or a laser (e.g. VCSEL)) and an eye tracking IR sensor 134B (e.g. IR camera, arrangement of IR photodetectors, or an IR position sensitive detector (PSD) for tracking glint positions). Wavelength selective filters 134C and 134D with representative reflecting element 134E implement bidirectional infrared (IR) filtering which directs IR illumination towards the eye 140, preferably centered about the optical axis 142 and receives IR reflections from the user eye 140, preferably including reflections captured about the optical axis 142, which are from the light guide optical element 112 to an IR sensor 134B.

In other embodiments, the eye tracking unit optics are not integrated with the display optics. For more examples of eye tracking systems for HMD devices, see U.S. Pat. No. 7,401,920, entitled "Head Mounted Eye Tracking and Display System", issued Jul. 22, 2008 to Kranz et al., see U.S. patent application Ser. No. 13/221,739, Lewis et al., entitled "Gaze Detection in a See-Through, Near-Eye, Mixed Reality Display," filed Aug. 30, 2011, and see U.S. patent application Ser. No. 13/245,700, Bohn, entitled "Integrated Eye Tracking and Display System," filed Sep. 26, 2011, all of which are incorporated herein by reference.

Opacity filter 114, which is aligned with light guide optical element 112, selectively blocks natural light from passing through light guide optical element 112 for enhancing contrast of virtual imagery. The opacity filter assists the image of a virtual object to appear more realistic and represent a full range of colors and intensities. In this embodiment, electrical control circuitry for the opacity filter, not shown, receives instructions from the control circuitry 136 via electrical connections routed through the frame. More details of an opacity filter are provided in U.S. patent application Ser. No. 12/887,426, "Opacity Filter For See-Through Mounted Display," filed on Sep. 21, 2010, incorporated herein by reference in its entirety.

Again, FIGS. 2A and 2B show half of the head mounted display device 2. For the illustrated embodiment, a full head mounted display device 2 may include another display optical system 14 with another set of optional see-through lenses 116 and 118, another opacity filter 114, another light guide optical element 112, as well as another image generation unit 120, another of outward facing capture devices 113, eye tracking system 134, and another of the earphones 130. In some embodiments, there may be a continuous display viewed by both eyes, rather than a display optical system for each eye. Additional details of a head mounted personal A/V apparatus are illustrated in U.S. patent application Ser. No. 12/905,952 entitled Fusing Virtual Content Into Real Content, Filed Oct. 15, 2010, fully incorporated herein by reference.

FIG. 3 is a block diagram of a system from a software perspective for providing a personalized sport performance experience with three dimensional (3D) virtual data being displayed by a near-eye, AR display of a personal audiovisual (A/V) apparatus. FIG. 3 illustrates an embodiment of a computing environment 54 from a software perspective which may be implemented by a system like personal A/V apparatus 8, one or more remote computer systems 12 in communication with one or more personal A/V apparatus or a combination of these. Additionally, personal A/V apparatus can communicate with other personal A/V apparatus for sharing data and processing resources. Network connectivity allows leveraging of available computing resources.

In this embodiment, software for a sport engine 414 may be executing on one or more processors of the personal A/V apparatus 8 for communicating with an image and audio processing engine 191 and perhaps other image capture devices like other 3D image capture devices 20 and other personal A/V apparatus 8 for exchanging and accessing data to personalize the user's sport performance experience. In the illustrated embodiment, a virtual data provider system 404 executing on a remote computer system 12 can also be executing a version 414N of the sport engine as well as other personal A/V apparatus 8 with which it is in communication for enhancing the experience.

The sport engine 414 accesses sport databases 329 for each sport supported. For example, the sport engine 414 may include a rule engine for each sport which accesses one or more rules stored in the databases 329. Some example of data stored in the sport databases 329 for a sport include rules for the sport, e.g. rules of the game, and recommendation rules for use by a recommendation engine included in the sport engine 414. For example, the rules for the sport may identify which types of kicks are allowed by an offense player, and the recommendation rules provide logic for determining which type of kick will be most effective for advancing the ball to the goal in the current context in a game.

Some other examples of data stored in the databases 329 include reference data for one or more physical sport movements associated with the sport, and execution criteria for the one or more associated movements. In some examples, the reference data for a physical sport movement is gesture filter (see below) which may be registered with the gesture recognition engine so it can notify the sport engine when a movement has occurred. Execution criteria may be reference image data or structural data (e.g. skeletal data) of a movement. In some instances, the reference image data is for a generic human within a range of physical characteristics. In other examples, such reference image data can be tailored to an individual based on the physical characteristics of the specific user. In other examples, the execution criteria may include relationships of body parts in a movement and ranges of distance and direction for each body part associated with the movement. Age may also be a factor of the execution criteria.

Another example of data stored in the databases may be how skill levels are defined with respect to satisfaction of the execution criteria. For example, some actions like keeping your eye on the ball within a movement, like a golf swing, may have a higher priority in satisfying execution criteria than other actions like how high the club is swung. Criteria for assigning skill levels may be stored as well. For example, there may be criteria for categorizing a sport movement performance as bad, good, excellent or beginner, intermediate, pro, and there may also be criteria by which an overall skill level is assigned for a user. Skills data for a particular user may be stored in user profile data 197, 322.

Another example of data which may be stored in the sport databases 329 are object properties for predetermined visual guides or previously generated visual guides and rule logic for selection and when to display one or more visual guides.

Another example of data which may be stored in the sport databases 329 is sport performance data for avatars generated by the sport engine, for example for a coach avatar, a generic skill level avatar, an avatar of the user, or a celebrity avatar. Some examples of sport performance data are motion capture data or image data from a prior performance. Other examples are accessible physics models for sport movements performed by the avatar, e.g. how the avatar runs, dunks a basketball, or several styles of serving a tennis ball. Sport performance data may also be stored for the user and be accessible via user profile data. Additionally, object properties like color, shape, facial features, clothing, and the like may be stored for an avatar for the virtual data engine 195 (see below) to access when displaying the avatar.

As shown in the embodiment of FIG. 3, the software components of a computing environment 54 comprise the image and audio processing engine 191 in communication with an operating system 190. Image and audio processing engine 191 processes image data (e.g. moving data like video or still), and audio data in order to support applications executing for a head mounted display (HMD) device system like a personal A/V apparatus 8 including a near-eye, augmented reality display. Image and audio processing engine 191 includes object recognition engine 192, gesture recognition engine 193, virtual data engine 195, eye tracking software 196 if eye tracking is in use, an occlusion engine 302, a 3D positional audio engine 304 with a sound recognition engine 194, a scene mapping engine 306, and a physics engine 308 which may communicate with each other.

The computing environment 54 also stores data in image and audio data buffer(s) 199. The buffers provide memory for receiving image data captured from the outward facing capture devices 113, image data captured by other capture devices if available, image data from an eye tracking camera of an eye tracking system 134 if used, buffers for holding image data of virtual objects to be displayed by the image generation units 120, and buffers for both input and output audio data like sounds captured from the user via microphone 110 and sound effects for an application from the 3D audio engine 304 to be output to the user via audio output devices like earphones 130.

Image and audio processing engine 191 processes image data, depth data and audio data received from one or more capture devices which may be available in a location. Image and depth information may come from the outward facing capture devices 113 captured as the user moves his head or body and additionally from other personal A/V apparatus 8, other 3D image capture devices 20 in the location and image data stores like location indexed images and maps 324.

The individual engines and data stores depicted in FIG. 3 are described in more detail below, but first an overview of the data and functions they provide as a supporting platform is described from the perspective of an application like the sport engine 414. The sport engine 414 executing in the personal A/V apparatus 8 or executing remotely on a computer system 12 for the personal A/V apparatus 8 leverages the various engines of the image and audio processing engine 191 for implementing its one or more functions by sending requests identifying data for processing and receiving notification of data updates. For example, notifications from the scene mapping engine 306 identify the positions of virtual and real objects at least in the display field of view. The sport engine 414 identifies data to the virtual data engine 195 for generating the structure and physical properties of an object for display. The sport engine 414 may supply and identify a physics model for each virtual object generated for its application to the physics engine 308, or the physics engine 308 may generate a physics model based on reference properties stored for an object in structure data 200.

The operating system 190 makes available to applications which gestures the gesture recognition engine 193 has identified, which words or sounds the sound recognition engine 194 has identified, the positions of objects from the scene mapping engine 306 as described above, and eye data such as a position of a pupil or an eye movement like a blink sequence detected from the eye tracking software 196. A sound to be played for the user in accordance with the sport engine 414 can be uploaded to a sound library 312 and identified to the 3D audio engine 304 with data identifying from which direction or position to make the sound seem to come from. The device data 198 makes available to the sport engine 414 location data, head position data, data identifying an orientation with respect to the ground and other data from sensing units of the display device 2.

The scene mapping engine 306 is first described. A 3D mapping of the display field of view of the augmented reality display can be determined by the scene mapping engine 306 based on captured image data and depth data. The depth data may either be derived from the captured image data or captured separately. The 3D mapping includes 3D space positions or position volumes for objects. A 3D space is a volume of space occupied by the object. Depending on the precision desired, the 3D space can match the 3D shape of the object or be a less precise bounding volume around an object like a bounding box, a bounding 3D elliptical shaped volume, a bounding sphere or a bounding cylinder. A 3D space position represents position coordinates for the boundary of the volume or 3D space. In other words the 3D space position identifies how much space an object occupies and where in the display field of view that occupied space is. As discussed further below, in some examples the 3D space position includes additional information such as the object's orientation.

A depth map representing captured image data and depth data from outward facing capture devices 113 can be used as a 3D mapping of a display field of view of a near-eye AR display. As discussed above, a view dependent coordinate system may be used for the mapping of the display field of view approximating a user perspective. The captured data may be time tracked based on capture time for tracking motion of real objects. Virtual objects can be inserted into the depth map under control of an application like sport engine 414. Mapping what is around the user in the user's environment can be aided with sensor data. Data from an orientation sensing unit 132, e.g. a three axis accelerometer and a three axis magnetometer, determines position changes of the user's head and correlation of those head position changes with changes in the image and depth data from the outward facing capture devices 113 can identify positions of objects relative to one another and at what subset of an environment or location a user is looking.

Depth map data of another HMD device, currently or previously in the environment, along with position and head orientation data for this other HMD device can also be used to map what is in the user environment. Shared real objects in their depth maps can be used for image alignment and other techniques for image mapping. With the position and orientation data as well, what objects are coming into view can be predicted as well so physical interaction processing, occlusion and other processing can start even before the objects are in view.

The scene mapping engine 306 can also use a view independent coordinate system for 3D mapping, and a copy of a scene mapping engine 306 may be in communication with other scene mapping engines 306 executing in other systems (e.g. 12, 20 and 8) so the mapping processing can be shared or controlled centrally by one computer system which shares the updated map with the other systems. Image and depth data from multiple perspectives can be received in real time from other 3D image capture devices 20 under control of one or more network accessible computer systems 12 or from one or more personal A/V apparatus 8 in the location. Overlapping subject matter in the depth images taken from multiple perspectives may be correlated based on a view independent coordinate system and time, and the image content combined for creating the volumetric or 3D mapping of a location (e.g. an x, y, z representation of a room, a store space, or a geofenced area). Thus, changes in light, shadow and object positions can be tracked. The map can be stored in the view independent coordinate system in a storage location (e.g. 324) accessible as well by other personal A/V apparatus 8, other computer systems 12 or both, be retrieved from memory and be updated over time. (For more information on collaborative scene mapping between HMDs like apparatus 8 and computer systems 12 with access to image data, see "Low-Latency Fusing of Virtual and Real Content," having U.S. patent application Ser. No. 12/912,937 having inventors Avi Bar-Zeev et al. and filed Oct. 27, 2010 and which is hereby incorporated by reference.)

When a user enters a location or an environment within a location, the scene mapping engine 306 may first query networked computer systems (e.g. 12 or 8) or a network accessible location like location indexed images and 3D maps 324 for a pre-generated 3D map or one currently being updated in real-time which map identifies 3D space positions and identification data of real and virtual objects. The map may include identification data for stationary objects, objects moving in real time, objects which tend to enter the location, physical models for objects, and current light and shadow conditions as some examples.

The location may be identified by location data which may be used as an index to search in location indexed image and 3D maps 324 or in Internet accessible images 326 for a map or image related data which may be used to generate a map. For example, location data such as GPS data from a GPS transceiver of the location sensing unit 144 on the display device 2 may identify the location of the user. In another example, a relative position of one or more objects in image data from the outward facing capture devices 113 of the user's personal A/V apparatus 8 can be determined with respect to one or more GPS tracked objects in the location from which other relative positions of real and virtual objects can be identified. Additionally, an IP address of a WiFi hotspot or cellular station to which the personal A/V apparatus 8 has a connection can identify a location. Additionally, identifier tokens may be exchanged between personal A/V apparatus 8 via infra-red, Bluetooth or WUSB. The range of the infra-red, WUSB or Bluetooth signal can act as a predefined distance for determining proximity of another user. Maps and map updates, or at least object identification data may be exchanged between personal A/V apparatus via infra-red, Bluetooth or WUSB as the range of the signal allows.

The scene mapping engine 306 identifies the position and orientation and tracks the movement of real and virtual objects in the volumetric space based on communications with the object recognition engine 192 of the image and audio processing engine 191 and one or more executing applications generating virtual objects like the sport engine 414.

The object recognition engine 192 of the image and audio processing engine 191 detects, tracks and identifies real objects in the display field of view and the 3D environment of the user based on captured image data and captured depth data if available or determined depth positions from stereopsis. The object recognition engine 192 distinguishes real objects from each other by marking object boundaries and comparing the object boundaries with structural data. Colors may also be detected as well, and shapes and surfaces derived. One example of marking object boundaries is detecting edges within detected or derived depth data and image data and connecting the edges. A polygon mesh may also be used to represent the object's boundary. The object boundary data is then compared with stored structure data 200 in order to identify a type of object within a probability criteria. Besides identifying the type of object, an orientation of an identified object may be detected based on the comparison with stored structure data 200.

For real objects, data may be assigned for each of a number of object properties 320 like 3D size, 3D shape, type of materials detected, color(s), and boundary shape detected. In one embodiment, based on a weighted probability for each detected property assigned by the object recognition engine 192 after comparison with reference properties, the object is identified and its properties stored in object properties data 320N.

One or more databases of structure data 200 accessible over one or more communication networks 50 may include structural information about objects. As in other image processing applications, a person can be a type of object, so an example of structure data is a stored skeletal model of a human which may be referenced to help recognize body parts. Structure data 200 may also include structural information regarding one or more inanimate objects in order to help recognize the one or more inanimate objects, some examples of which are furniture, sporting equipment, automobiles and the like.

The structure data 200 may store structural information such as structural patterns for comparison and image data as references for pattern recognition. The image data may also be used for facial recognition. The object recognition engine 192 may also perform facial and pattern recognition on image data of the objects based on stored image data from other sources as well like user profile data 197 of the user, other users profile data 322 which are permission and network accessible, location indexed images and 3D maps 324 and Internet accessible images 326. Motion capture data from image and depth data may also identify motion characteristics of an object. The object recognition engine 192 may also check detected properties of an object like its size, shape, material(s) and motion characteristics against reference properties stored in structure data 200.

The reference properties may have been predetermined manually offline by an application developer or by pattern recognition software and stored. Additionally, if a user takes inventory of an object by viewing it with the personal A/V apparatus 8 and inputting data in data fields, reference properties for an object can be stored in structure data 200 by the object recognition engine 192. The reference properties (e.g. structure patterns and image data) may also be accessed by applications for generating virtual objects.

There may also be stored in structure data 200 a physics parameters data set for an object. Some example physics parameters include a mass range for the type of object, one or more inner material type(s), a modulus of elasticity for use with Hooke's Law, one or more tensile strengths associated with one or more material types including at least a surface material type, and a surface coefficient of friction associated with the surface material. Air may be considered a type of inner material. These parameters may be selected for a physics model representing an object for use by a physics engine 308 as discussed below.

The scene mapping engine 306 and the object recognition engine 192 exchange data which assist each engine in its functions. For example, based on an object identification and orientation determined by the object recognition engine 192, the scene mapping engine 306 can update a 3D space position or position volume for an object for more accuracy. For example, a chair on its side has different position coordinates for its volume than when it is right side up. A position history or motion path identified from position volumes updated for an object by the scene mapping engine 306 can assist the object recognition engine 192 track an object, particularly when it is being partially occluded.

Upon detection of one or more objects by the object recognition engine 192, image and audio processing engine 191 may report to operating system 190 an identification of each object detected and a corresponding 3D space position which may include object orientation which the operating system 190 passes along to other executing applications like the scene mapping engine 306, the occlusion engine 302, the physic engine 308 and other upper level applications 166 like the sport engine 414.

The gaze or point of gaze of a user may be determined based on eye tracking data from the eye tracking system 134 and the 3D mapping of the display field of view by one or more processors of the personal A/V apparatus 8 executing the eye tracking software 196. In one example of determining gaze, the eye tracking software 196 executing on the one or more processors identifies a pupil position within each eye and models a gaze line for each eye extending from an approximated location of a respective fovea. The 3D scene mapping engine 306 executing on the one or more processors determine a position in the display field of view where the gaze lines meet. This intersection is the point of gaze and it is within the Panum's fusional area for human eyes which is the area in which objects are in focus. Based on the 3D mapping of objects in the display field of view, a current object or point in a location at which the gaze lines meet is a current object or point of focus.

The occlusion engine 302 identifies spatial occlusions between objects, and in particular between real and virtual objects based on spatial position data for recognized objects within a coordinate system as updated by the objection recognition engine 192 and the scene mapping engine 306. For more information about occlusion processing, see U.S. patent application Ser. No. 12/905,952 entitled "Fusing Virtual Content into Real Content," Flaks et al., and filed Oct. 15, 2010, which is hereby incorporated by reference and see also U.S. patent application Ser. No. 13/443,368 entitled "Realistic Occlusion for a Head Mounted Augmented Reality Display" Geisner et al., and filed Apr. 10, 2012, which is hereby incorporated by reference.

The 3D audio engine 304 is a positional 3D audio engine which receives input audio data and outputs audio data for the earphones 130 or other audio output devices like speakers in other embodiments. The received input audio data may be for a virtual object or be that generated by a real object. Audio data for virtual objects generated by an application or selected from a sound library 312 can be output to the earphones to sound as if coming from the direction of the virtual object. An example of a positional 3D audio engine which may be used with an augmented reality system is disclosed in U.S. patent application Ser. No. 12/903,610 entitled "System and Method for High-Precision 3-Dimensional Audio for Augmented Reality," to Flaks et al., and filed Oct. 13, 2010, which is hereby incorporated by reference.

Sound recognition engine 194 of the 3D audio engine identifies audio data from the real world received via microphone 110 for application control via voice commands and for environment and object recognition. Based on a sound library 312, the engine 304 can identify a sound with a physical object, e.g. a crack of a bat, a golf ball hit in the sweet spot, a tennis ball hit with the rim of the racket, etc. Additionally, voice data files stored in user profile data 197 or user profiles 322 may also identify a speaker with whom a person object mapped in the environment may be associated.

An embodiment of a natural user interface (NUI) in one or more embodiments of the personal A/V apparatus 8 may include the outward facing capture devices 113 and the gesture recognition engine 193 for identifying a gesture which is an example of at least one user physical action of at least one body part. The eye tracking system 134 and the eye tracking software 196 for interpreting eye movements based on the data captured by the system 134 may also be components in another embodiment of a natural user interface for the personal A/V apparatus 8. Eye based actions like a blink sequence indicating a command, a gaze pattern, or gaze duration identified by the eye tracking software 196 are also some examples of user input as one or more user physical actions of at least one body part. The microphone and sound recognition engine 194 can also process natural user input of voice commands which may also supplement other recognized physical actions such as gestures and eye gaze.

The gesture recognition engine 193 can identify actions performed by a user indicating a control or command to an executing application. The action may be performed by a body part of a user, e.g. a hand or finger, but also an eye blink sequence of an eye can be a gesture. In one embodiment, the gesture recognition engine 193 includes a collection of gesture filters, each comprising information concerning a gesture that may be performed by at least a part of a skeletal model. The gesture recognition engine 193 compares a skeletal model and movements associated with it derived from the captured image data to the gesture filters in a gesture library to identify when a user (as represented by the skeletal model) has performed one or more gestures. In some examples, matching of image data to image models of a user's hand or finger during gesture training sessions may be used rather than skeletal tracking for recognizing gestures.

More information about the detection and tracking of objects can be found in U.S. patent application Ser. No. 12/641,788, "Motion Detection Using Depth Images," filed on Dec. 18, 2009; and U.S. patent application Ser. No. 12/475,308, "Device for Identifying and Tracking Multiple Humans over Time," both of which are incorporated herein by reference in their entirety. More information about the gesture recognition engine 193 can be found in U.S. patent application Ser. No. 12/422,661, "Gesture Recognizer System Architecture," filed on Apr. 13, 2009, incorporated herein by reference in its entirety. More information about recognizing gestures can be found in U.S. patent application Ser. No. 12/391,150, "Standard Gestures," filed on Feb. 23, 2009; and U.S. patent application Ser. No. 12/474,655, "Gesture Tool," filed on May 29, 2009, both of which are incorporated by reference herein in their entirety.

The physics engine 308 simulates the physics of motion of objects and the exchange of energy between objects as forces are applied to them based on rules governing a physical environment. In other words, the physics engine 308 helps make collisions between objects look real. The term "collision" in this specification is used in a physics sense of the word meaning a physical contact during which at least portions of different objects meet, and each object exerts a force upon the other causing an exchange of energy. For example, a handshake with a virtual person is a collision which can be modeled. A real object (e.g. a hand) collision with a virtual object, and a virtual object collision with another virtual object can be modeled by the physics engine 308. In the illustrative examples discussed herein, Newton's laws of physics are used as the illustrative rules for a physical environment. An application can define different physical environment rules. For example, an environment having a different gravitational force than Earth's can be requested by inputting different environmental parameters.

Physics engine libraries 328 are used by the physics engine 308 in updating physics models and simulating actions and effects like collision effects, sound effects and visual effects. Some examples of physics engine libraries 328 are as follows. One or more materials lookup tables in the libraries 328 can be referenced by the physics engine 308 for identifying physics parameters like tensile strength and coefficients of friction for different types of materials. A pre-collision events library includes data for representing events or actions, for example a gesture, which signal or trigger a collision. For example, an object landing on a certain area in an environment may be a trigger for an explosion. The sport engine 414 can register pre-collision events with the physics engine 308.

An action simulator library includes software instructions for simulating movement of at least a part of an object based on input parameters of one or more physical properties. The sport engine 414 can register simulated actions for avatars with the physics engine 308 for use in an interactive avatar mode. A collision effects library comprises software routines for simulating a change in at least one physical property of an object during or resulting from a collision based on different input parameters. For example, a collision effect may be a change in surface shape of an object to the collision. Other examples are different crack patterns or different breaking patterns for different materials or the same material in different orientations.

The sound library 312, besides being a resource for command and object recognition based on sound, may also store audio data for sound effects (e.g. crack of a bat, puck hitting a side of a rink) to be played by the 3D audio engine 304 and which may be linked with different simulated actions, pre-collision events and collision effects. Audio models for contact sounds and other sports related audio sounds may also have been registered by the sport engine 414 with the physics engine 308 as sound effects for types of virtual equipment. Similarly, a visual effects library may store routines for animations, highlighting, and other types of visual enhancements which may also be associated with particular actions, pre-collision events and collision effects.

The libraries 328 also store previously generated or stored virtual objects physics models and real objects physics models. Persistent object identifiers may be associated with the physics models so once a real object is recognized as a previously recognized object, the physics model can be retrieved from storage rather than regenerated to save time. Similarly, virtual objects previously registered by one or more applications, for example via a software interface like an application programming interface (API), can be retrieved from the library as well. A plurality of physics models may be associated with an object. For example, there may be a library of physics models for actions, including sport performance movements, associated with an avatar. For more information, see U.S. patent application Ser. No. 13/458,800 to inventors Daniel J. McCulloch et al. entitled "Displaying a Collision between Real and Virtual Objects," filed on Apr. 27, 2012 and which is incorporated by reference herein in its entirety.

An application like sport engine 414 communicates data with the virtual data engine 195 in order for the virtual data engine 195 to display and update display of one or more virtual objects controlled by the application 166.

Virtual data engine 195 processes virtual objects and registers the 3D position and orientation of virtual objects or imagery in relation to one or more coordinate systems, for example in view dependent coordinates or in the view independent 3D map coordinates. The virtual data engine 195 determines the position of virtual data in display coordinates for each display optical system 14. Additionally, the virtual data engine 195 performs translation, rotation, and scaling operations for display of the virtual data at the correct size and perspective. A virtual data position may be dependent upon, a position of a corresponding object, real or virtual, to which it is registered. The virtual data engine 195 can update the scene mapping engine about the positions of the virtual objects processed.

The following discussion describes some example processing for updating an optical see-through, augmented reality display to position virtual objects so that they appear realistically at 3D locations determined for them in the display. In one example implementation of updating the 3D display, the virtual data engine 195 renders the previously created three dimensional model of the display field of view including depth data for both virtual and real objects in a Z-buffer. The real object boundaries in the Z-buffer act as references for where the virtual objects are to be three dimensionally positioned in the display as the image generation unit 120 displays the virtual objects but not real objects as the display device is an optical see-through display device. For a virtual object, the virtual data engine 195 has a target 3D space position of where to insert the virtual object.

A depth value is stored for each display element or a subset of display elements, for example for each pixel (or for a subset of pixels). Virtual data corresponding to virtual objects are rendered into the same z-buffer and the color information for the virtual data is written into a corresponding color buffer. The virtual data includes any modifications based on collision processing. In this embodiment, the composite image based on the z-buffer and color buffer is sent to image generation unit 120 to be displayed at the appropriate pixels. The display update process can be performed many times per second (e.g., the refresh rate). For a video-see, augmented reality display or operation of a see-through display in a video-see mode, image data of the real objects is also written into the corresponding color buffer with the virtual objects. In a video-see mode, the opacity filter of each see-through display optical system 14 can be tuned so that light reflected from in front of the glasses does not reach the user's eye 140 and the 3D image data of both the real and virtual objects is played on the display.

Device data 198 may include an identifier for the personal apparatus 8, a network address, e.g. an IP address, model number, configuration parameters such as devices installed, identification of the operating system, and what applications are available in the personal A/V apparatus 8 and are executing in the personal A/V apparatus 8 etc. Particularly for the see-through, augmented reality personal A/V apparatus 8, the device data may also include data from sensors or sensing units or determined from the sensors or sensing units like the orientation sensors in inertial sensing unit 132, the microphone 110, and the one or more location and proximity transceivers in location sensing unit 144.

User profile data, in a local copy 197 or stored in a cloud based user profile 322 has data for user permissions for sharing or accessing of user profile data and other data detected for the user like location tracking, objects identified which the user has gazed at, biometric data or determined states of being of the user. Besides personal information typically contained in user profile data like an address and a name, physical characteristics for a user are stored as well. As discussed in more detail below, physical characteristics include data such as physical dimensions some examples of which are height and weight, width, distance between shoulders, leg and arm lengths and the like.

Figure 4:
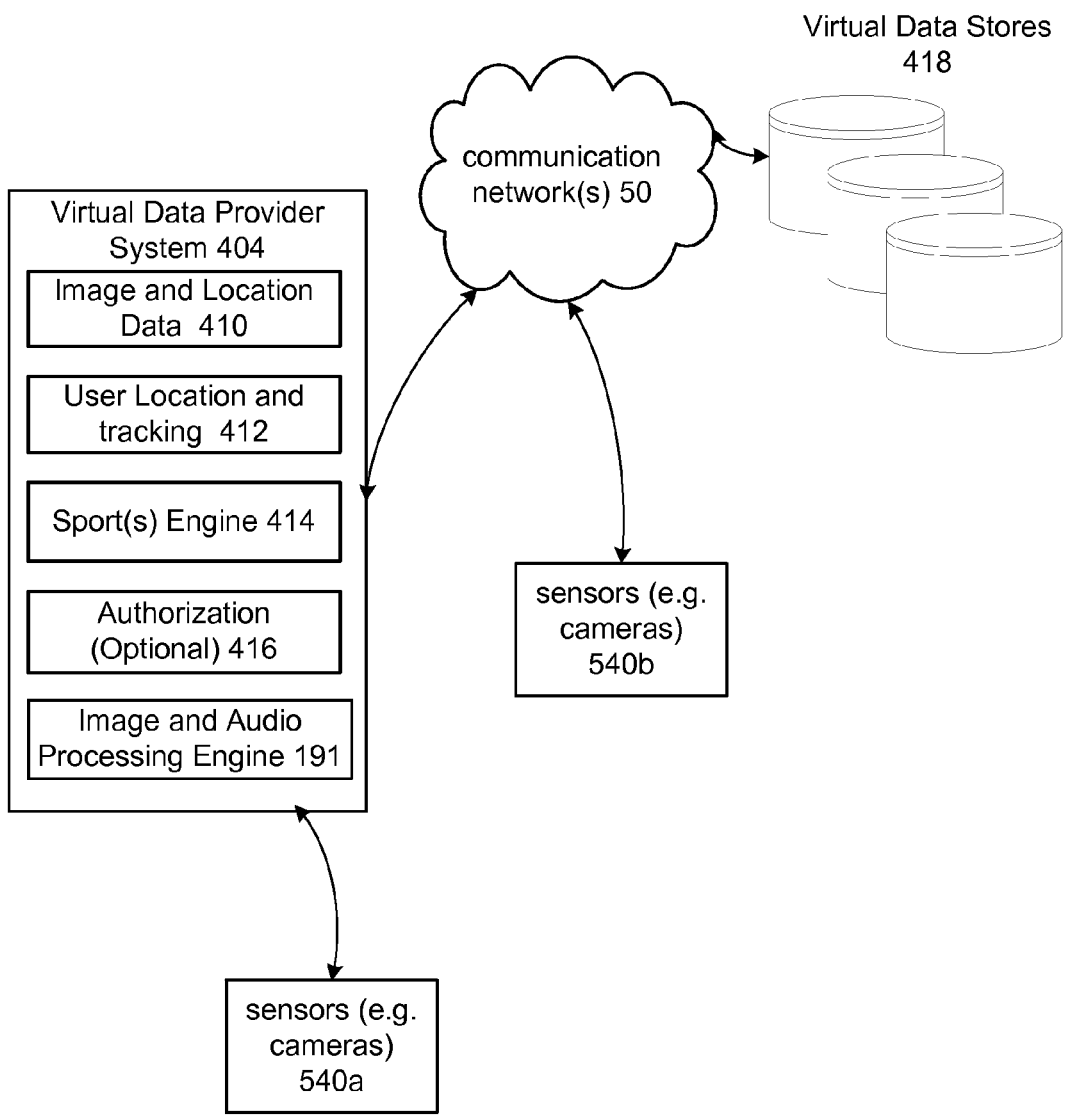
FIG. 4 is a block diagram of an embodiment of a virtual data provider system.

FIG. 4 is a block diagram of an embodiment of a virtual data provider system which shows an example architecture for one or more processes and/or software running on a virtual data provider system 404. Virtual data provider system 404 has access to virtual data stores 418 which store virtual data, including 3D virtual data. This data may be, for example, sports performance data or data used to generate a display of sports performance data for an avatar. Another example may be display data for generating one or more visual guides including 3D virtual data. In this embodiment, at least one virtual data provider system 404 is associated with each location. Additionally, the virtual data provider system stores location data 410 for identifying its location such as GPS data, IP data or other device data which identifies its position within the location. Another type of location data 410 is image data captured of the location, and in some examples captured depth data of the location. As discussed further below, the image data of the real objects in the location is captured from a plurality of perspectives. In one embodiment, 3D image capture devices 20 are placed around the sport performance areas at the location for capturing a 360 degree view, and in some cases a 360 degree view at various heights for image data within a cylinder. Image data from capture devices 113 on different personal A/V apparatus in the vicinity of the sport performance area may also provide image data of real objects.

The virtual data provider system 404 receives location data from personal A/V apparatus in the location and tracks the location, or position within a real physical location of one or more users with a user location and tracking module 412. Virtual data is made available for download by the apparatus 8 based on one or more objects or areas around a user in a user's location. Optionally an authorization component 416 is included to authenticate the user in the location.

The virtual data provider system 404 includes a version of an image and audio data processing engine 191 as a platform supporting the sport engine 414 in servicing one or more personal A/V apparatus 8 which may be being used throughout the performance location. For example, a scene mapping engine 306 for the virtual data provider system tracking a view independent 3D mapping of objects, including object identifiers for users in the location, the real objects, and the virtual objects and effects being displayed in the location. Additionally, the virtual data engine 195 of the provider system can provide processing resources to assist the personal A/V apparatus 8 update their display fields of view more quickly. For example, the remote virtual data engine 195 can format the virtual data in a standardized holographic format which is downloaded and readily displayed by the personal A/V apparatus 8.

In this example, a virtual data provider 404 is communicatively coupled to a set of one or more sensors 540 either directly, 540a, or over a communication network 50 like sensor 540b. Some examples of sensors include video sensors, depth image sensors, heat sensors, IR sensors, weight sensors, motion sensors, etc. In this example, the respective sensors are used to track the personal A/V apparatus within the respective location for tracking where the user is and also capture image and depth data of the site throughout the day for tracking environmental conditions like weather and obstacles. Additionally, there may be sensors included with the sports equipment (e.g. ball, club, bat, etc.) for tracking a position in the location and orientation of the sports equipment with respect to one or more body parts of the user for providing data for analyzing an execution quality of a movement. In some examples, either or both of the personal A/V apparatus 8 or a virtual data provider 404 has a receiver (e.g. wireless transceiver 137) for receiving the sensors data of the user in the location, from the sports equipment or both.

The technology may be embodied in other specific forms without departing from the spirit or essential characteristics thereof. Likewise, the particular naming and division of modules, routines, applications, features, attributes, methodologies and other aspects are not mandatory, and the mechanisms that implement the technology or its features may have different names, divisions and/or formats.

For illustrative purposes, the method embodiments below are described in the context of the system and apparatus embodiments described above. However, the method embodiments are not limited to operating in the system and apparatus embodiments described above and may be implemented in other system and apparatus embodiments. Furthermore, the method embodiments may be continuously performed while the personal A/V apparatus is in operation and an applicable application is executing.

Figure 5:
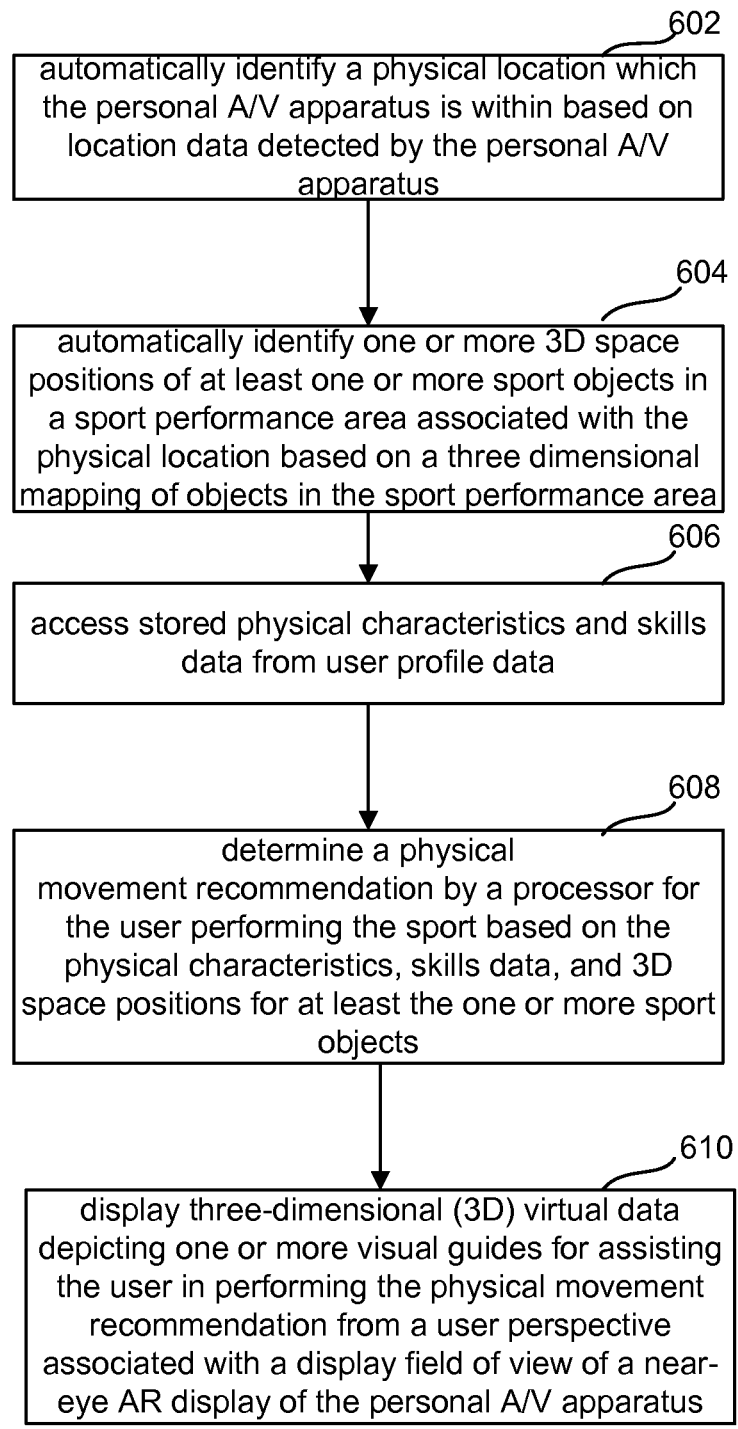
FIG. 5 is a flowchart of an embodiment of a method for providing a personalized sport performance experience with three dimensional (3D) virtual data displayed by a near-eye, AR display of a personal A/V apparatus.

FIG. 5 is a flowchart of an embodiment of a method for providing a personalized sport performance experience with three dimensional (3D) virtual data displayed by a near-eye, augmented reality display of a personal A/V apparatus. In step 602, the scene mapping engine 306 automatically identifies a real physical location in which the personal A/V apparatus is within based on location data detected by the personal A/V apparatus. For example, the scene mapping engine 306 may identify the physical location based on GPS data stored in the device data 198. Additionally, an IR transceiver of the location sensing unit 144 may have established a communication link with a sensor communicatively coupled to a virtual data provider system 404 and receives location identifying data from the virtual data provider system. In another example, image data detected or captured by the image capture devices 113 is uploaded to a virtual data provider system 404 executing on a network accessible computer system 12, which identifies the location in the image data based on stored image data, and notifies the scene mapping engine 306, which in turn notifies one or more applications like the sport engine 414 executing on the personal A/V apparatus of the location.

In step 604, the scene mapping engine 306 automatically identifies 3D space positions of at least one or more sport objects, real or virtual, in a sport performance area associated with the physical location based on a three dimensional mapping of objects in the sport performance area. In some embodiments, the scene mapping engine 306 notifies the sport engine 414 of the identified 3D space positions of the one or more sport objects. An example of a sport object is sports equipment, some examples of which are a football or baseball, bat, club, goal post, hockey net, golf hole and flag. Another example of a sport object is another player. In other embodiments, the sport engine is programmed to check the 3D mapping based on a programmed trigger like a time interval or data update notice. The sport engine database may have made accessible reference structures for one or more sports objects (e.g. a basketball, a basketball hoop and a backboard) based on the sports applications supported by the engine. Besides sport objects, the sport engine 414 may also check for objects not related to the sport for purposes such as safety warnings due to objects which may pose obstacles outside the context of the sport and also to check environmental conditions and the confines of a sport performance area in a physical location. The sport performance area in the physical location may be a virtual representation of a sport performance area displayed by the AR display or a real sport performance area like a field, court, or course.

In one embodiment, the sport engine 414 may be executing software for providing recommendations for performing a physical sport movement. The recommendations may be provided automatically or responsive to user input requesting a recommendation. For example, a user may have selected automatic recommendations by making a finger pointing gesture at a menu item in a menu displayed by the near-eye AR display or may request a recommendation by audio command of saying "recommendation" which is captured by the microphone 110 and processed by the speech recognition engine and forwarded to the sport engine. A recommendation may be personalized by factoring in the user's abilities as well as the context parameters, e.g. distance of a ball from a goal, of the current play. In step 606, the sport engine 414 accesses stored physical characteristics and skills data from user profile data stored for the user, for example in network accessible user profile data 322 accessible to the sport engine.

Physical characteristics include data such as physical dimensions some examples of which are height and weight, width, distance between shoulders. Some physical characteristics may have been input by the user like height and weight. A characteristic like height may be determined based on inertial sensing data from the inertial sensing unit 132 and perhaps reference image data as the user wears the near-eye display on his head. In some instances image data of the user captured by another user's apparatus 8 or data sharing cameras like image sensors 540, which may include 3D image capture devices 20, in the real physical location may also be a source for identifying physical characteristics. Some other examples of physical characteristics are widths, lengths and ratios for upper and lower legs, widths, lengths and ratios for upper and lower arm parts. Based on performance data stored for previous executions of sports movements, a strength rating may be assigned for a user's arms and legs, as part of their physical characteristics.

In step 608, the sport engine 414 determines a physical movement recommendation by a processor for the user performing the sport based on the accessed physical characteristics, skills data and 3D space positions for at least the one or more sports objects. In some embodiments, the 3D space position of an object which is not related to the sport may be a basis for the determination as well. As discussed below, FIG. 6 provides an example of a process for determining a physical movement recommendation.

In step 610, 3D virtual data depicting one or more visual guides for assisting the user in performing the physical movement recommendation is displayed from a user perspective associated with a display field of view of the near-eye AR display. A user moves around typically when playing a sport or sport objects, real or virtual, move with respect to the user. The scene mapping engine 306 identifies a change in the display field of view and updates the displaying of 3D virtual data based on the change in the display field of view. Additionally, the sport engine 414 notifies the scene mapping engine 306 of changes effecting the position of virtual data it generates in the course of the sport performance session like changes in direction and speed of objects and removal and appearance of visual guides. The scene mapping engine 306 updates the 3D mapping based on these changes.

As mentioned above in the embodiment of FIG. 3, the sport engine accesses stored rules for a sport. Some examples of rules are those by which points are scored, minimum parameters for a sport performance area or sport performance location, physical sport movements available to different player positions, (e.g. catcher, pitcher, quarterback, etc.), within different zones of the performance location, and at different time periods in the course of a game, e.g. overtime.

Figure 6:
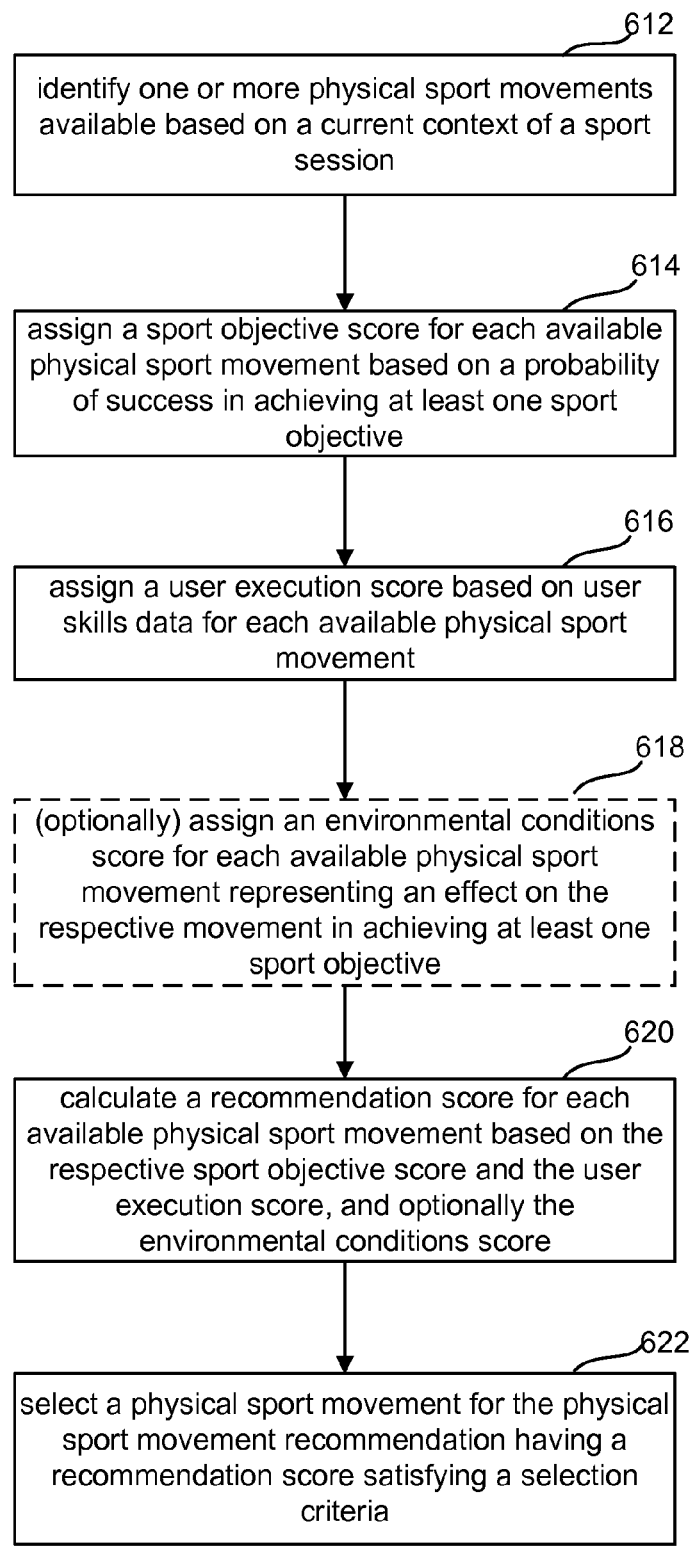
FIG. 6 is a flowchart of some exemplary steps of determining a physical movement recommendation by a processor for the user.

FIG. 6 is a flowchart of some exemplary steps of determining a physical movement recommendation by a processor for the user. In step 612, the sport engine identifies one or more physical sport movements available based on a current context of a sport session. Some examples of data making up the current context of the sport session are the user's current role in the sport session, (e.g. quarterback, defensive lineman, pitcher, hitter, etc.), allowed movements for the role, one or more positions of any other players in the session, skill levels of any other player, a current score, a current time period or place in a sequence of play or performance, e.g. how far has the user runner run already, the $9^{th}$ inning or the $4^{th}$ inning, $4^{th}$ hole or $18^{th}$ hole, etc., and a distance and direction of a scoring sports object like a ball or puck or the user holding the scoring sports object to the scoring zone, e.g. goal, hole, etc. In some examples, such information can be obtained from monitoring the display field of view of the near-eye AR display. For example, the user tends to look at the hole or the flag where the golf hole is, the basketball net is, the soccer goal is and the like. A distance and direction can be calculated based on the user's position on the golf course, court, field, etc. from location data, head position data, and image data of the image capture devices 113. In an example, where the personal A/V apparatus 8 does not have access to data from other image capture devices, non-image sensor data such as on the sport objects can provide position data for tracking sport movements and sports objects, particularly with use of the 3D mapping. In other examples, image data shared by other apparatus 8 or capture devices 20, 540 in the physical location can be checked for verifying position data.

In step 614, the sport engine includes a recommendation engine which processes the recommendation rules in the databases 329, and assigns a sport objective score for each available physical sport movement based on a probability of success in achieving at least one sport objective. Some examples of sport objectives are advancing the runner, increasing running speed, and blocking an opponent's ball. Objectives are sport specific. In some examples, a weighted value may be assigned to each available movement representing its probability of success. The different objectives may also be weighted based on the current context of the performance session as well and factored into the objective score for each movement.

In step 616, the sport engine assigns a user execution score based on user skills data for each available physical sport movement. For example, again weights may be assigned. A person may have good execution skills with a seven iron in golf but not with lower numbered irons and woods, so a golf swing with a seven iron may receive a higher execution score than a golf swing with a three iron. The sport objective score however for the seven iron is lower than the three iron in an example context in which the distance to the hole is about 250 yards.

In optional step 618, the sport engine may assign an environmental conditions score for each available physical sport movement representing an effect on the respective movement in achieving at least one sport objective. For example, wind conditions may increase or decrease the projected speed of a ball like a football or a golf ball. In an example where the player is playing in a real sport performance area, sensors 540 may include sensors for detecting environmental conditions like weather conditions. In a virtual environment sport performance session using a virtual sport performance area, a user may have selected conditions like rain or snow or wind to be implemented during the session.

In step 620, the sport engine calculates a recommendation score for each available physical sport movement based on the respective sport objective score and the user execution score, and optionally the environmental conditions score. For example, in some embodiments, the weighted scores may simply be added to calculate a recommendation score, and the movement with the highest score selected as the physical movement recommendation. How recommendations are calculated is a matter of design choice. For example, other steps may be included such as randomly deleting one recommendation score or one objective score to avoid repetitive recommendations in similar situations.

In step 622, the sport engine selects a physical sport movement for the physical sport movement recommendation having a recommendation score satisfying a selection criteria. For example, as mentioned in the discussion of step 620, the selection criteria may be a highest combined score of the objective and user execution scores. In other examples, the selection criteria may be different based on how the logic embodied in the sport engine assigns weights or otherwise designates priorities among factors.

Some examples of information a physical sport movement recommendation may include are a type of movement, what piece of sports equipment to use, a direction of aim, a position on a field or court at which to perform the movement, a suggested body movement (e.g. duck, run, throw, run and reach for a fly ball, move back and bend down to catch a ball), and a strength to use for a movement. The physical sport movement is sport dependent. For example, a golf physical sport movement may include a club recommendation and a direction of aiming the golf ball, which may not be directly at the hole depending on the obstacles like a pond or sand trap in the way and the user's abilities identified in his skills data.

In some basketball examples, the recommendation may include one or more movements such as dribbling to a spot or zone of the court and taking a basketball shot from there with a medium strength. An alternative may be a jump shot in a zone farther from the basket with a high strength designation. For example, a bunt swing in baseball is different from a baseball swing typically used to get a hit. A basketball dunk shot recommendation may be for one hand or for two hands and the hand or hands are near the top of the ball as the user is typically very near the basket. A recommendation for a shot a further distance from the basket may indicate hand placement near the middle of the ball, and a recommendation of taking a shot at the basket from the opponent's court side may indicate or the hands are near the bottom to keep the ball in the air for the longer distance. In another example, the angle at which the quarterback holds the ball is different for a long pass down the field than for a short lateral to a receiver or a hand-off for a ground play.

As illustrated in later figures, the recommendation may also include execution tips personal to the user in the form of displayed visual guides which help the user in executing one or movements by a body part designated in the physical movement recommendation. The visual guides may be image data of the user's own body part or parts which the user can place his or her one or more actual body parts over and follow for executing the movement.

Figure 7:
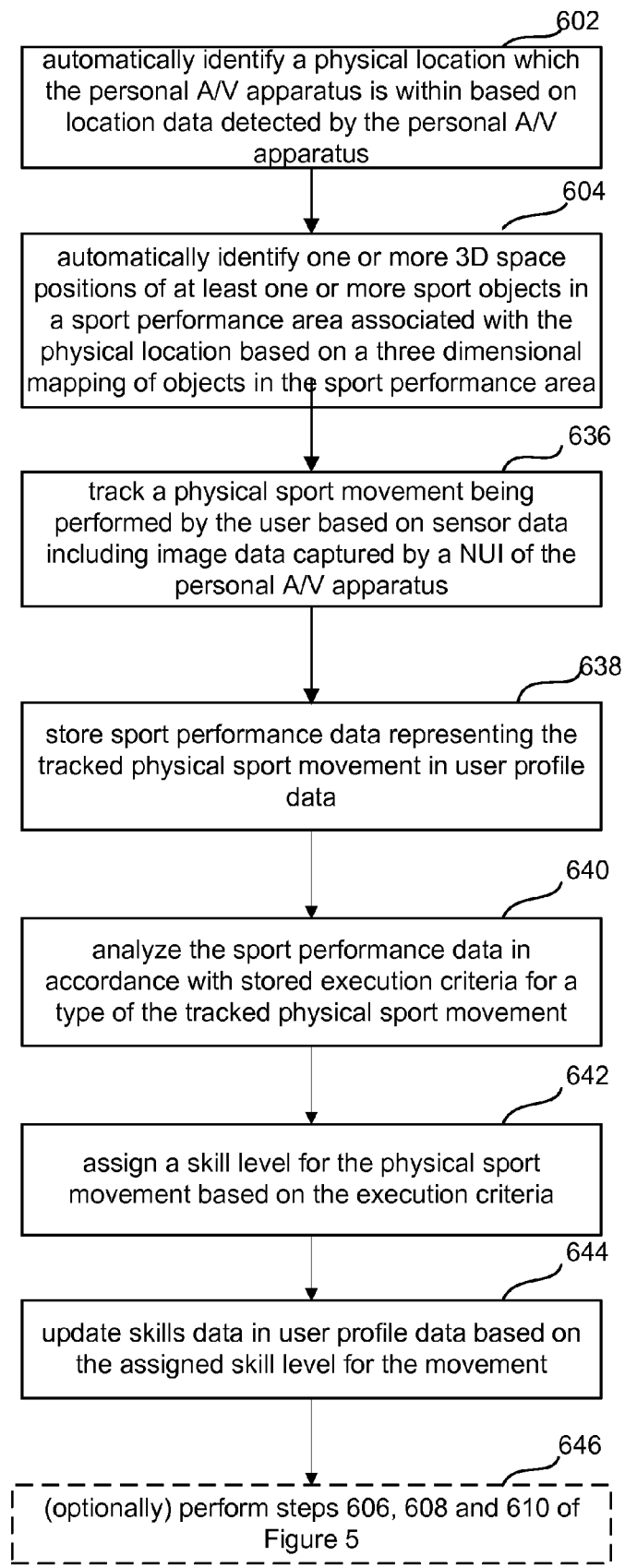
FIG. 7 is a flowchart of another embodiment of a method for providing a personalized sport performance experience with three dimensional (3D) virtual data displayed by a near-eye, AR display of a personal A/V apparatus.

FIG. 7 is a flowchart of another embodiment of a method for providing a personalized sport performance experience with three dimensional (3D) virtual data displayed by a near-eye, augmented reality display of a personal A/V apparatus. In the embodiment of a method, steps 602 and 604 may be performed as discussed with respect to FIG. 5.

In step 636, the sport engine tracks a physical sport movement being performed by the user based on sensor data including image data captured by a natural user interface (NUI) of the personal A/V apparatus and in step 638 stores sports performance data representing the tracked physical sport movement in user profile data.

For example, in the embodiment of FIG. 3, the sport engine 414 may track a physical sport movement being performed by the user. The sport engine may make filters available to the gesture recognition engine to use in identifying one or more physical sport movements associated with the sport and notifying the sport engine. In some embodiments, the sport engine stores image data of the movement or a motion capture file derived from image data (e.g. skeletal model of movement) as sports performance data for the user. In an example where the user is using a real sport object, the motion of the real sport object set in motion by the actual physical movement of the user can be tracked based on sensor data, virtual data is displayed illustrating the tracked motion of the real sport object. The same motion tracking and display of the path of motion of a virtual sport object may also be displayed.

In step 638, the sport engine stores sport performance data representing the tracked physical sport movement in user profile data, and in step 640, the sport engine analyzes the sport performance data in accordance with stored execution criteria for a type of the tracked physical sport movement.

In some examples, execution criteria may be embodied as skeletal reference models or image data of skill level representative executions of the physical sport movement for the user's physical characteristics. The captured image or image derived data can be compared against the execution criteria models for a closest match in some examples. The differences of one or more body parts from a model for a movement can be measured and identified as falling within one or more ranges. In some examples, the differences may be defined in terms of 3D distance, angular rotation, or 3D direction differences between the user's body part and the same type of body part represented in the model. Stored execution criteria can have predetermined difference ranges for one or more body parts. In some examples, based on which body parts fall within which predetermined difference ranges, an execution quality score and a skill level for the movement can be assigned. An overall skill level for the user may be assigned based on an accumulation of skill levels assigned for various movements associated with a sport. Some examples of skill levels are beginner, intermediate, and expert.

Particularly in embodiments in which the portable personal A/V apparatus is operating without image data from other cameras at predetermined positions for capturing a user from angles outside the display field of view, for example a 360 degree arrangement of cameras, determining execution quality of a movement can be based on image data of the display field of view, as well as non-image sensed data like audio data, gaze data, orientation data, the 3D mapping, and sensor data on the sport equipment if available. For example, in golf, an example of a physical sport movement is a golf swing. A golfer tends to look at the golf ball. Anything a user looks at, image capture devices 113 captures as well, at least in most sports situations. An inertial sensing unit 132 can approximate how far the user's head is from the ball, and such inertial data can also refine or update a distance determined from the front captured image data. Furthermore, an orientation of the near-eye, augmented reality (AR) display can be determined, for example based on date from the inertial sensing unit 132.

A user also naturally tends to look at her hands on the club, so the sport engine can identify grip issues based on the image data. Gaze data can identify that the user took her eyes off the ball, and when during the swing, she did so. Golf in particular is a sport with audio sounds which identify how a club head met the ball in a swing. For example, "topping" the ball, as often occurs when one takes one's eyes off the ball, has an identifiable sound as does hitting the ball in the sweet spot of the club. A microphone of the personal A/V apparatus can capture a sound made in a physical location by a real sport object. The one or more processors are communicatively coupled to receive audio data representing the sound from the microphone and executes a sound recognition engine for identifying the sound as a sound related to the physical sport movement. The one or more processors compare the sound related to the physical movement against execution sound criteria for assigning a sound factor, e.g. a weighting, as part of execution criteria for analyzing the execution quality of a swing and assigning a skill level for the physical sport movement.

The sports equipment like the ball or puck and other equipment like a club, bat, or hockey stick may also have sensors which provide data on their positions and contact points with other real objects, like clubs and bats, used by the user or in a physical sport performance location. Such sensor data can also be provided as bases to the sport engine for analyzing the physical sport movement in identifying things effecting execution quality like strength and direction of a swing based on where the ball landed and where contact was made with a bat or club or backboard.

In step 642, the sport engine assigns a skill level for the physical sport movement based on the execution criteria, and in step 644, the sport engine updates skills data in user profile data based on the assigned skill level for the movement. (See the discussion above for examples.) The skills data may be stored locally or in a network accessible memory like cloud based memory for storing user profile data 322. In step 646, the sport engine may also perform steps 606, 608 and 610 of FIG. 5 for providing a recommendation.

In some embodiments, the user may be using or playing with virtual sport objects like a virtual ball and virtual other players. The method embodiments discussed above may also comprise displaying from the user perspective motion of a virtual sport object responsive to the actual physical movement of the user. In other examples, the method embodiments like those in FIGS. 5 and 7 may also include the sport engine displaying a virtual sport performance area for the user performing the sport and determining the physical movement recommendation by the processor for the user based on one or more features in the virtual sport performance area. For example, a user may be playing with real or virtual sports equipment in his living room, but based on the 3D virtual data displayed by his near-eye AR display, he is playing at a famous golf course where a well-known annual tournament occurs.

Before discussing enhancing a sport experience with display of avatars, audio data can also be used to provide feedback on execution quality when performing a sport with virtual sports equipment. The sport databases 329 may also include a contact sound for a virtual sport object. The one or more processors (e.g. 210 or 902 of companion processing module 4) of the personal A/V apparatus 8 may determine audio parameters for a contact sound for a virtual sport object contacted in the physical sport movement based on the sports performance data captured and analyzed for the physical sport movement. The 3D audio engine 304 can generate and play the contact sound related to the physical sport movement in accordance with the audio parameters determined for the contact sound through one or more audio output device, e.g. earphones 130, of the personal A/V apparatus.

Figure 8A:
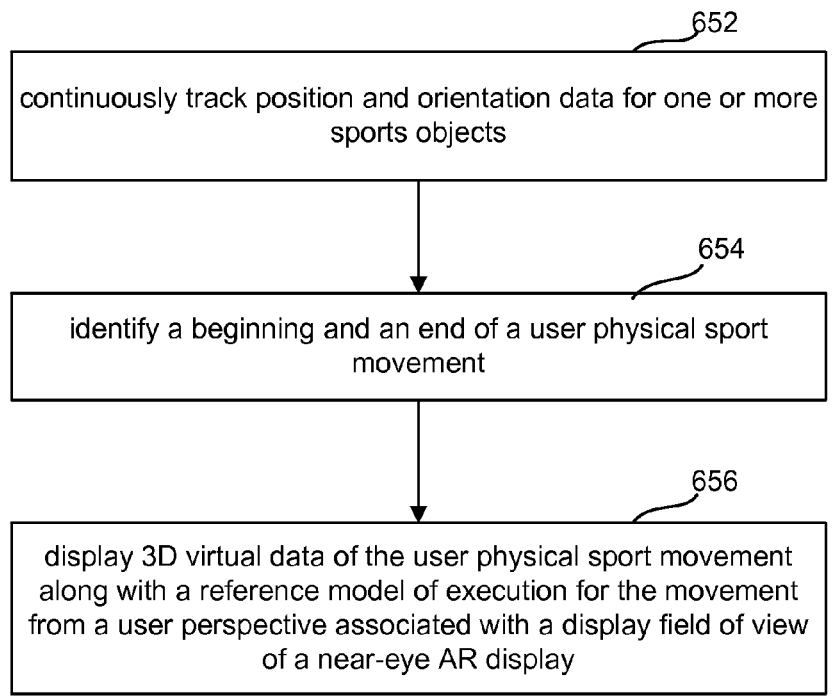
FIG. 8A is a flow chart of an embodiment of a method for providing visual feedback from a user perspective for a physical sport movement.

FIG. 8A is a flow chart of an embodiment of a method for providing visual feedback from a user perspective for a physical sport movement. After a user has completed a physical sport movement, she may like to see an "instant replay" or visual representation. Additionally, seeing her movement from her perspective against a reference model of execution recommended for the motion may also be helpful. In the illustrative context of FIG. 3, the sport engine 414 in step 652 continuously tracks position and orientation data for one or more sport objects. For example, the sport engine 414 can receive 3D space position data including orientation data for a club or bat a user is holding from the scene mapping engine 306. The object recognition engine 192 may have processed image and depth data not only from image capture devices 113 but also from other capture devices (20, 540, 113s of other personal A/V 8) having the user in their field of view when performing the movement. Additionally, there may be non-image sensor data available such as from the inertial sensing unit 132 on the personal A/V apparatus 8 and on the sports objects like a ball and a club. Such sensors (e.g. 540) may be include one or more contact sensors for identifying touch or contact where contact was made with a piece of sport equipment, IR or GPS sensors for position in a sport performance area, and one or more inertial sensors. For example, a golf club face may have an inertial sensor which identifies its position with respect to a reference point, e.g. the ground.

In step 654, the sport engine 414, or the gesture engine 193 based on filters registered by the sport engine 414 as mentioned above, identifies a beginning and an end of a user physical sport movement. The different aspects of a physical movement may not all be captured by the outward facing capture devices 113. Image data from different perspectives and sensor data with different reference points may be available. Such data is used by the sport engine 414 to transform 3D virtual data representing a sport object or a user body part in the movement to a coordinate system so the 3D virtual representation appear to the user from his or her perspective as approximated by the near-eye AR display. Image data of a user's hands, lower arms and golf club captured by capture devices 113 in a first time period of a swing, may be used in the visual feedback with transparent color data for a reference model. Image data from a camera opposite the front of the user may capture the club, arm and shoulder movements outside the field of view of the devices 113. Such supplemental image data may be transformed to keep the motion of the club and body parts, but from a user perspective, to display the motion of the full swing from the user perspective associated with the display field of view. In step 656 displays 3D virtual data of the user physical sport movement along with a reference model of execution for the movement from a user perspective associated with a display field of view of the near-eye AR display being worn by the user. Such visual feedback will help a user with the form of her golf swing. The user can move her head and follow the motion of her swing and the visual guides depicting the reference model of execution from her perspective as if making the swing in her near-eye AR display. The reference model of execution may be generated as visual guides based on a physical movement recommendation determined by the sport engine and selected by the user.

For example, after a golf swing, a user following her golf swing in her near-eye AR display, can see with her head and eyes FIG. 9F, discussed below, also illustrates an example of post movement visual feedback for a golf swing.

Performing a sport with an avatar can definitely enhance a sport performing experience. For example, playing against an avatar of oneself or even just seeing one's prior performance on a previous trek or golf course can be educational. Additionally, while really playing in one's living room but virtually at a selected sport performance location or at an actual physical sport performance location which is where tournaments have taken place, it may be fun to see the prior performance of a celebrity as presented by that person's avatar playing with virtual equipment or even just captured video data for the same context point in the performance session, e.g. at the third hole. In some example, a prior sport performance may be selected to be performed by an avatar even if the user's sport performance area or location is not the same area or location where the prior sport performance occurred. For example, the user may be at a community basketball court and wishes to see a favorite celebrity's play.

It may even be more fun to interactively play with a celebrity. For example, a user at a neighborhood baseball field may select a virtual sport performance area or location of Yankee Stadium in 1956 to be overlaid on the real baseball field. The user may select a position to play in a pivotal game of the 1956 World Series between the Yankees and the Brooklyn Dodgers and play that player's role using virtual equipment. As discussed above, the sport engine may interface with a physics engine to cause avatars of the other players to perform the sports movements they were known to play in the game but also to perform a sport movement in response to the user's sports movements during the game. The user can see how the game would have been effected by his performance. In another example, the user can assemble a virtual "dream team" or "fantasy team" to play on in a session against another such team on which a real friend is playing. The sport engine predicts the actions of the dream team members based on performance data, skills data, or both stored for the dream team avatars.

In some examples, the avatar may be a virtual coach for whom audio and virtual data is displayed representing the coach as giving verbal and demonstrative instructions on physical movement recommendations.

In other examples, one person may be playing at a remote location location. For example, an avatar of a first player at a real course is displayed as 3D virtual data in the near-eye AR display of a second player in his living room which second player is playing on a virtual version of the real sport performance location (e.g. golf course or basketball court). In other examples, the virtual version of the real sport performance location may be displayed on a display separate from the near-eye AR display while visual guides for enhancing execution of a movement are displayed from the user perspective by the near-eye AR display. Similarly, an avatar of the second player may be displayed by the near-eye AR display of the first player, as if at the real sport performance location at a position in context with the game or performance, e.g. at the position where the second player's ball would have landed on the real course which is analogous to where his virtual ball was determined to land on the virtual version of the course. Other cameras in the remote location, such as a 3D image capture device, like that associated with a game console, and image capture devices in the real sport performance location, like those which may be communicating with a virtual data provider 404 may provide additional image data for enhancing the realism of the respective avatar mimicking the represented user's sports movements in real time.

In other examples, an avatar not associated with a specific person may be selected. For example, the sport engine 414 may provide a selection, e.g. a menu, of avatars for a highly skilled player, an intermediate player, an advanced beginner player and a beginner player from which a user can select an avatar to play against or watch performing similar movements as the user for skill improvement purposes.

Figure 8B:
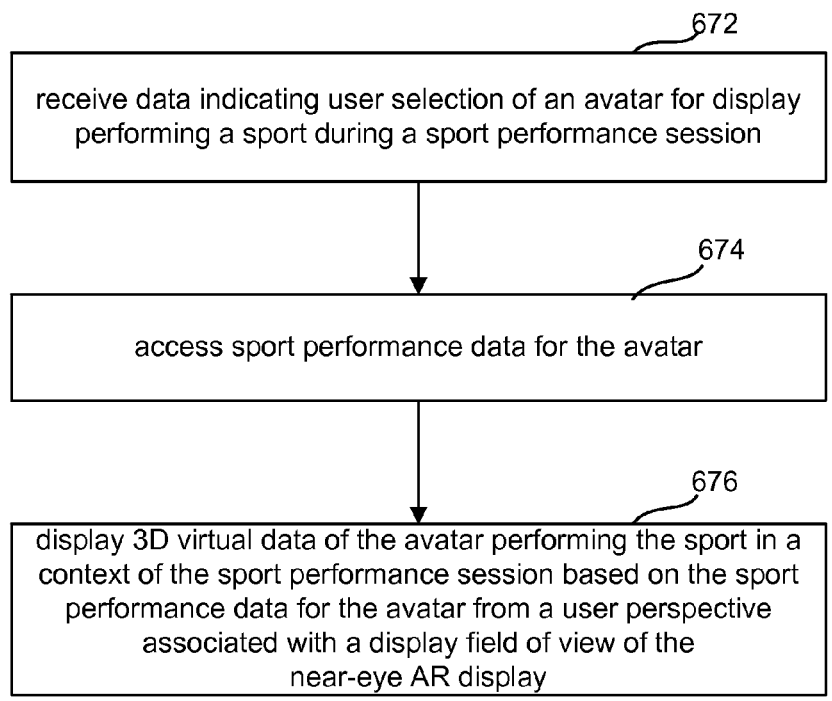
FIG. 8B is a flow chart of yet another embodiment of a method for providing a personalized sport performance experience with three dimensional (3D) virtual data displayed by a near-eye, AR display of a personal A/V apparatus.

FIG. 8B is a flow chart of yet another embodiment of a method for providing a personalized sport performance experience with three dimensional (3D) virtual data displayed by a near-eye, augmented reality (AR) display of a personal A/V apparatus. In step 672, the sport engine receives data indicating a user selection of an avatar for display performing a sport during a sport performance session. One or more user input devices, such as the NUI system, of the personal A/V apparatus can capture user input as discussed above and forwards data to the operating system which forwards the data to applications like the sport engine 414. In step 674, the sport engine accesses sport performance data for the avatar, and in step 676 displays 3D virtual data of the avatar performing the sport in the context of a sport performance session based on the accessed sport performance data for the avatar from a user perspective associated with a display field of view of the near-eye AR display.

Figure 9A:
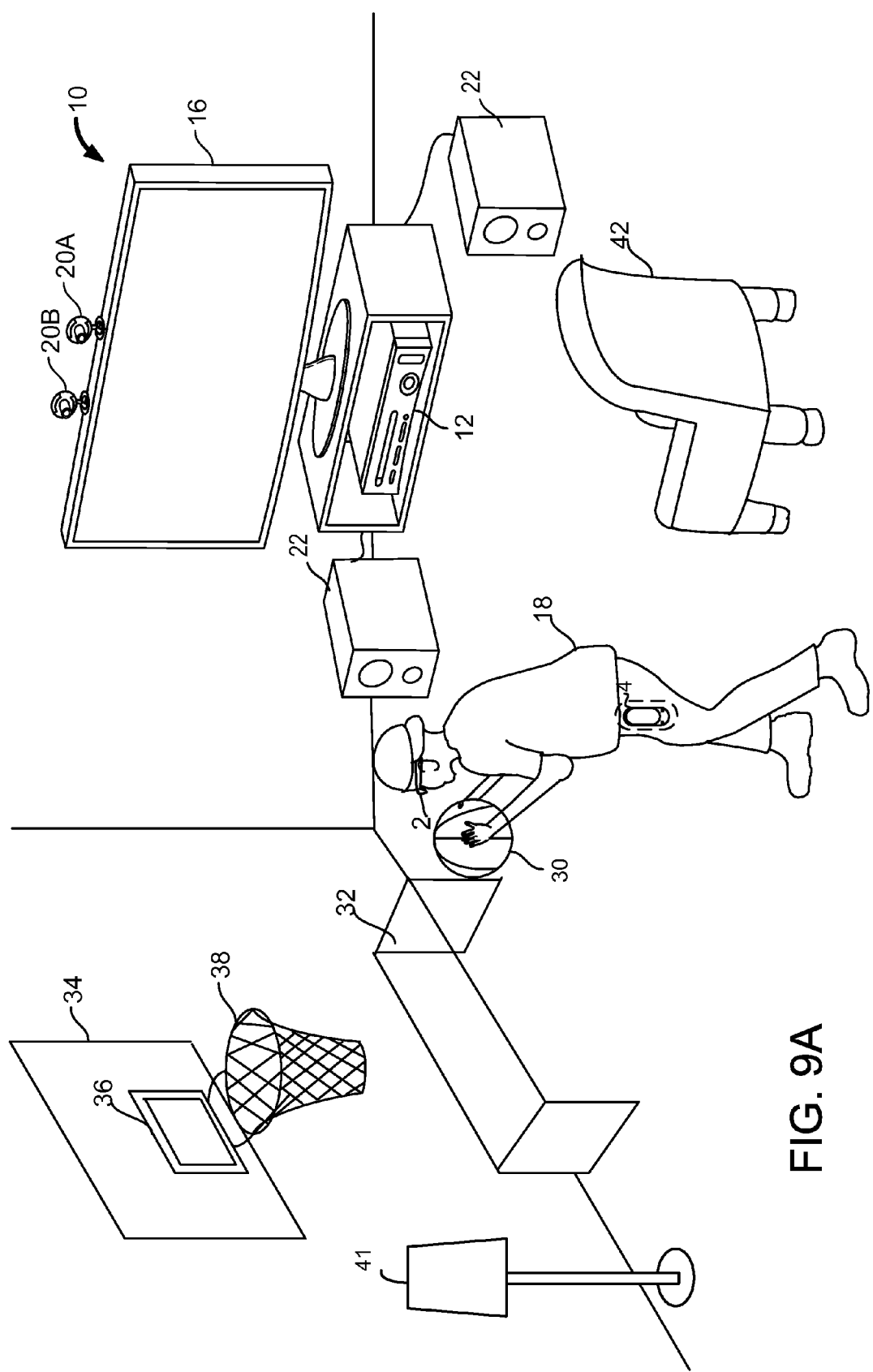
FIG. 9A illustrates a contextual example in which one or more embodiments of the technology may operate.

FIG. 9A illustrates a contextual example in which one or more embodiments of the technology may operate. A user 18, "Joe", is playing a virtual basketball application provided by the sport engine 414 in his living room. Chair 42, glass table 32, lamp 41, and home entertainment system 10 are real. The basketball backboard 34 with its box 36 and the basket or basketball hoop 38 are 3D virtual data projected by Joe's near-eye AR display device 2. The home entertainment system 10 includes a network accessible computer system 12 which in this example is a gaming console. Joe's processing unit 4 is embodied in a mobile smartphone in this example as well which communicates wirelessly with the gaming console and Joe's display device 2. In addition to a television 16 and speakers 22, the gaming console controls two depth cameras 20A and 20B for capturing image and depth data of the living room for a 3D mapping of the living room including real and virtual objects therein. The gaming console can communicate positions and object identification information to the processing unit 4 to cut down on processing time for the personal A/V apparatus (2 and 4). Processing unit 4 can also send image data of the display field of view of Joe's display device 2 to the gaming console.

Joe holds a virtual basketball 30 as he readies for a throw at the basket 38. Joe's holding of the basketball is a collision. Joe's hands apply forces on the ball 30 and the ball has reactive forces. The basketball application executing in Joe's personal A/V apparatus (e.g. 2 and 4) provides a physics model for each of the virtual objects it generates like the basketball 30, the basketball hoop 38 and the backboard 34 with box 36. The physics models for the real objects were derived from image data, any user provided information during any inventory, and object reference data stored in structure data 200.

Figure 9B:
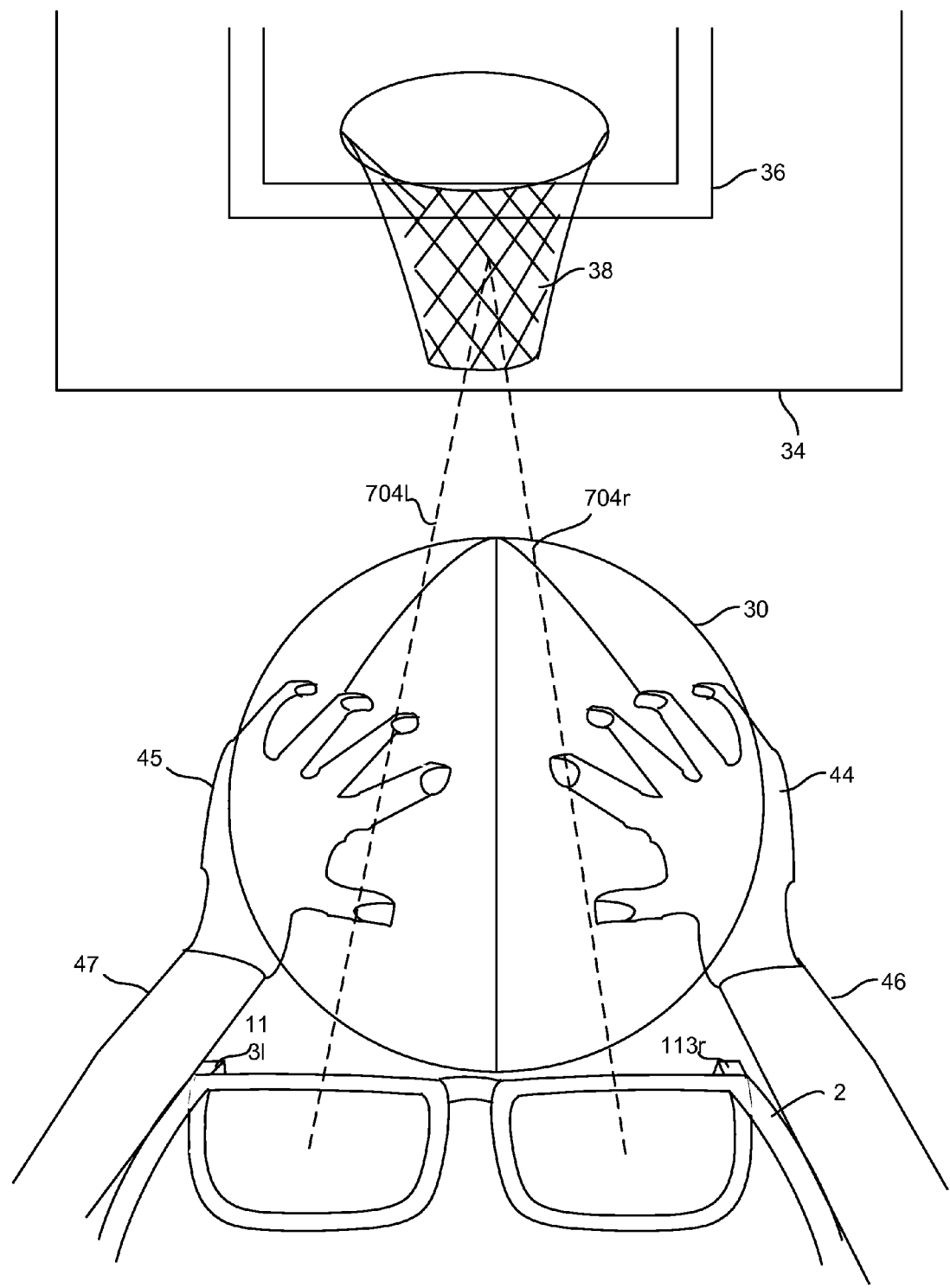
FIG. 9B illustrates an example of a user perspective associated with a display field of view which continues the example of FIG. 9A.

FIG. 9B illustrates a display field of a near-eye AR display worn by user Joe 18 playing basketball with a virtual ball and basketball hoop or basket in his living room in continuing the example of FIG. 9A. Based on the image data of the display field of view and the eye tracking system 134 as well as the scene mapping engine 306 processing and data provided by the eye tracking software 196, it can be identified that Joe is gazing, and thus will likely aim, at the middle of the basketball hoop 38, and Joe is in the process of throwing the ball with hands 45 and 44 positioned by his lower arms 47 and 46 near the center of the ball which will cause the ball to be thrown below the hoop as an analysis of the throw by the sport engine may indicate if Joe completes the throw.

As Joe contemplates making a throw, the image and audio processing engine 191 of the personal A/V apparatus updates the 3D mapping of Joe's living room to indicate Joe's distance and direction to the virtual basketball hoop 38 based on depth data captured by outwarding facing capture devices 113. The sport engine 414 identifies that based on the distance and direction of Joe to the hoop, a throw has an acceptable likelihood of increasing his score by making the basket based on, for example, recommendation rules as may be stored in sport databases 329.

The sport engine 414 identifies actions or movements which make up a throw movement and execution criteria to be met in order for the success of the throw. Some of the actions or movements which make up the throw movement are (1) directing one's gaze at the target position of the throw, (2) a distance to the target position, (3) a direction to the target throw, (4) position of the ball with respect to a reference point of the personal A/V apparatus approximating a reference point to a user body part or parts, and (5) hand positions on the ball. A recommendation of a throw at the basket is made with respect to Joe's physical characteristics, and visual guides are generated and displayed to assist Joe in performing the recommended throw.

Figure 9C:
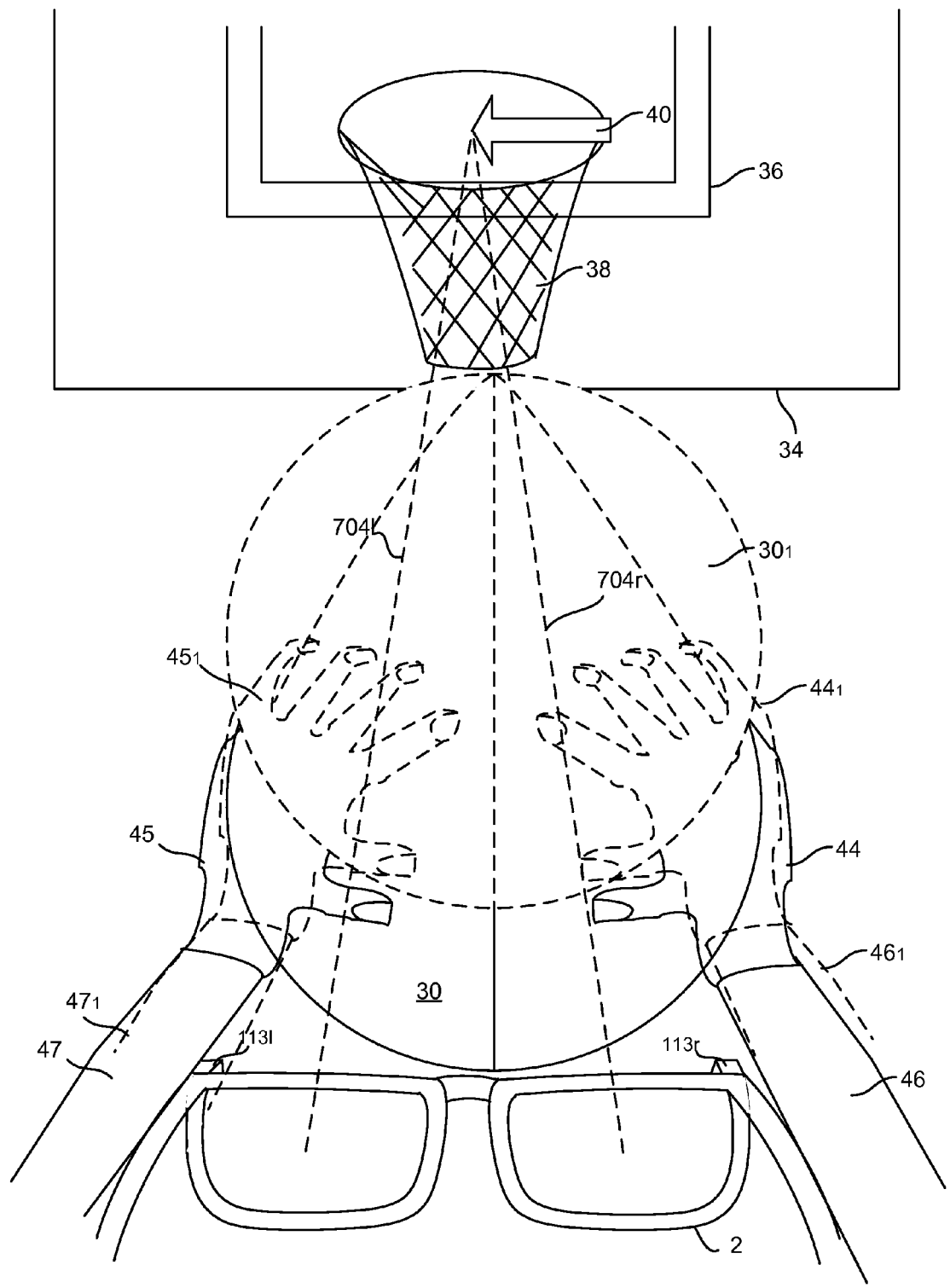
FIG. 9C illustrates an example of visual guides for assisting the user in performing the physical movement recommendation.

FIG. 9C illustrates an example of visual guides for assisting the user, in this case Joe, in performing the physical movement recommendation, in this case of a throw at the basket. One visual guide is arrow 40 which is displayed to directs Joe's gaze, and hence his aim, to the space above the basket 38. 3D Virtual data generated based on image data of Joe's own hands is displayed to guide Joe to positions his hands like his own projected hands seen from his perspective. Joe is in a good position from the basket. 3D virtual data of a virtual version $30_1$ of Joe's basketball provides a visual guide of where to position his basketball for making the shot. Virtual guide versions $44_1$, $45_1$ of Joe's hands 44 and 45 and virtual guide versions $46_1$, $47_1$ of his lower arms 46, 47 are projected for Joe from his perspective to illustrate the recommendation of how he position his hands on the basketball at its recommended position.

Figure 9D:
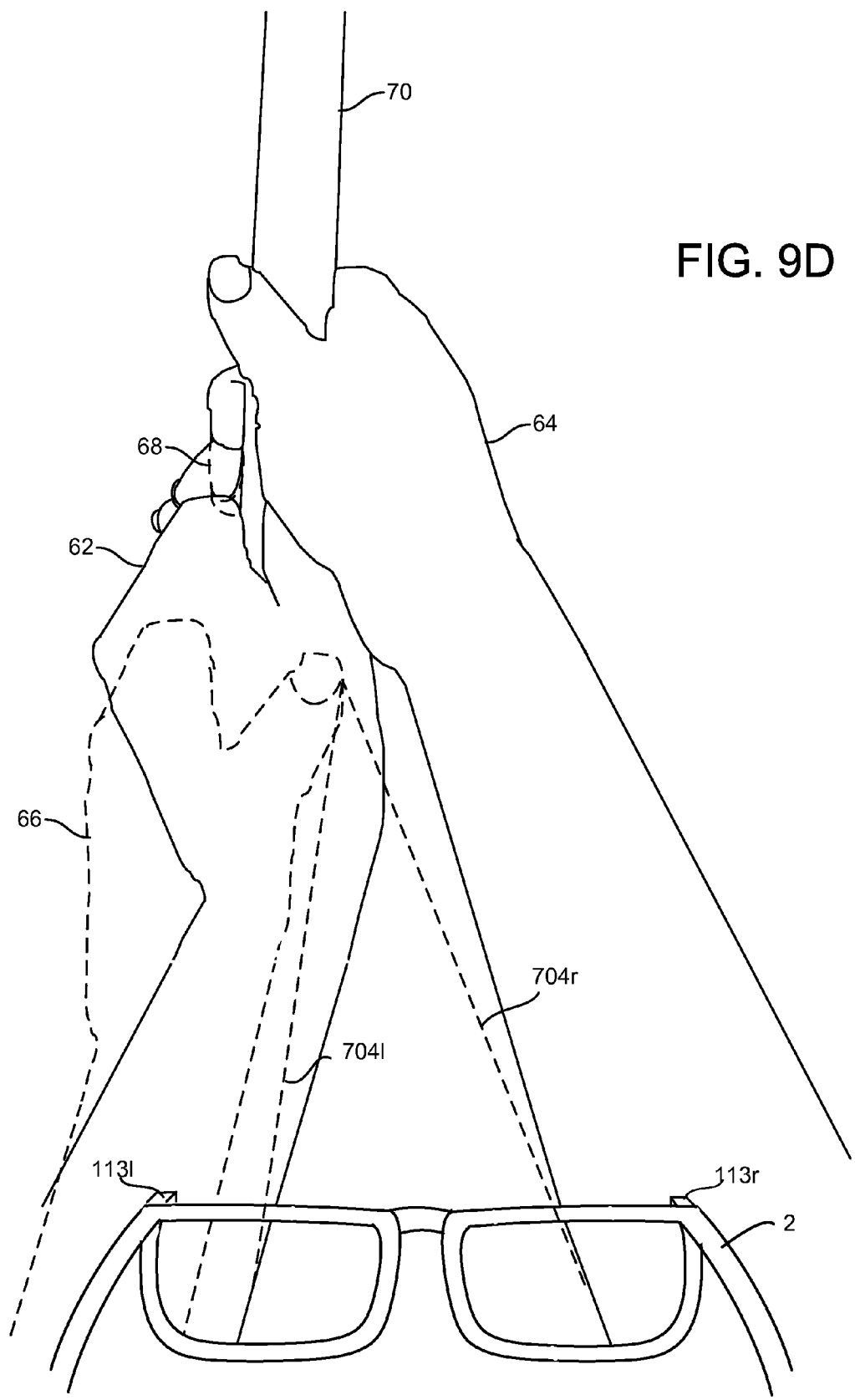
FIG. 9D illustrates another example of a visual guide for assisting the user in performing a physical movement.

FIG. 9D illustrates another example of a visual guide for assisting the user in performing a physical movement, gripping a golf club 70 in this example. For the current context of a seven iron recommendation or the user selection of the seven iron, the sport engine 414 identifies in the display field of view captured by the outward facing image capture devices 113, which also capture depth in this example, that the user right hand 64 and user left hand 62 are gripping a seven iron slightly to the left of the user's center which is correct. However, based on the distance to the hole, a more open grip meaning the left hand would rotate to the left is determined as a recommendation. Additionally, the grip recommendation may include a recommendation of moving the left hand 66 up the golf club toward the user. A virtual 3D version of a hand, and preferably, the user's hand is displayed as a visual guide 66 to assist the user in moving her left hand to the recommended grip position. 3D virtual data represents a visual guide 68 showing the recommended positions of the fingers of the right hand 64 for the recommended grip position. In this example, the user wearing near-eye, AR display device 2 gazes, see illustrative gaze lines **704*l* and 704*r* at the new thumb position. In some examples, the visual guides may be highlighted outlines, of one or more body parts or other types of guides like navigational aids (e.g. arrows). A guide for at least one body part may be transparent but colored to help the user fit at least one body part into the recommended position. The guide may be displayed as flashing or highlighted when the sport engine 414** determines the user has positioned the at least one body part in satisfaction of criteria for the recommendation, and may then disappear.

In many embodiments, the sport engine 414 updates a physical movement recommendation in real time based on a change in the sport context such as a user electing not to follow the recommendation, another player has moved the ball, or environmental conditions have changed such as an obstacle has entered the sport performance area. As in the grip example, if the user rejects a club recommendation and chooses another club, the sport engine 414 updates its recommendation with updated grip advice for the user club selection which advice may be displayed visually using a visual guide.

Figure 9E:
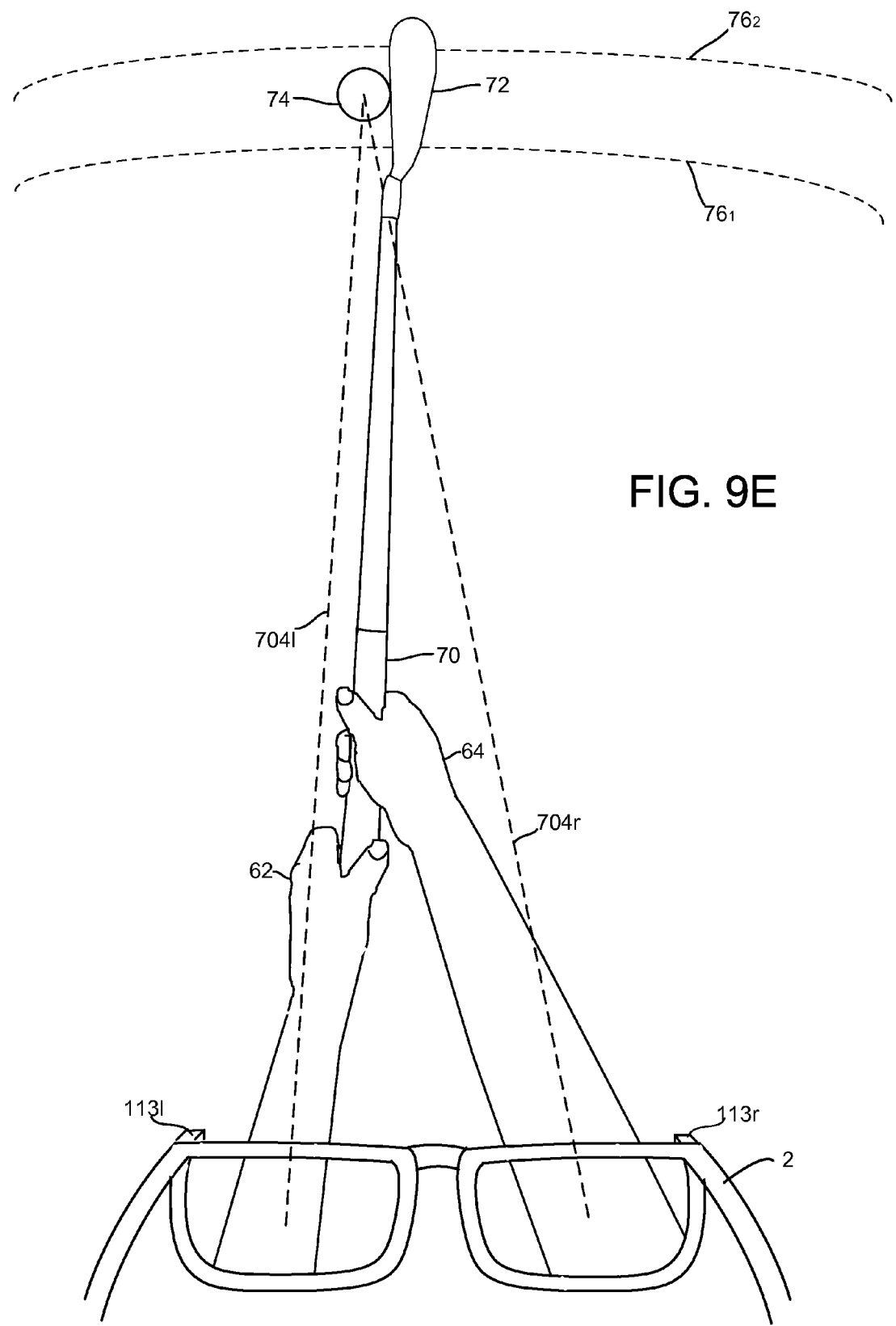
FIG. 9E illustrates another example of a display field of view of a contextual example of a user addressing a golf ball.

FIG. 9E illustrates another example of a display field of view of a contextual example of a user addressing a golf ball. In FIG. 9E, the user has positioned his hands 62 and 64 in the recommended grip position and move his head to focus on the position of ball 74 as indicated by gaze lines **704*l* and 704*r*. The club head 72** of the seven iron is positioned against the ball in the middle of a swing path outlined by visual guides $76_1$ and $76_2$. For example, the visual guides may be lines displayed in a fluorescent color.

Figure 9F:
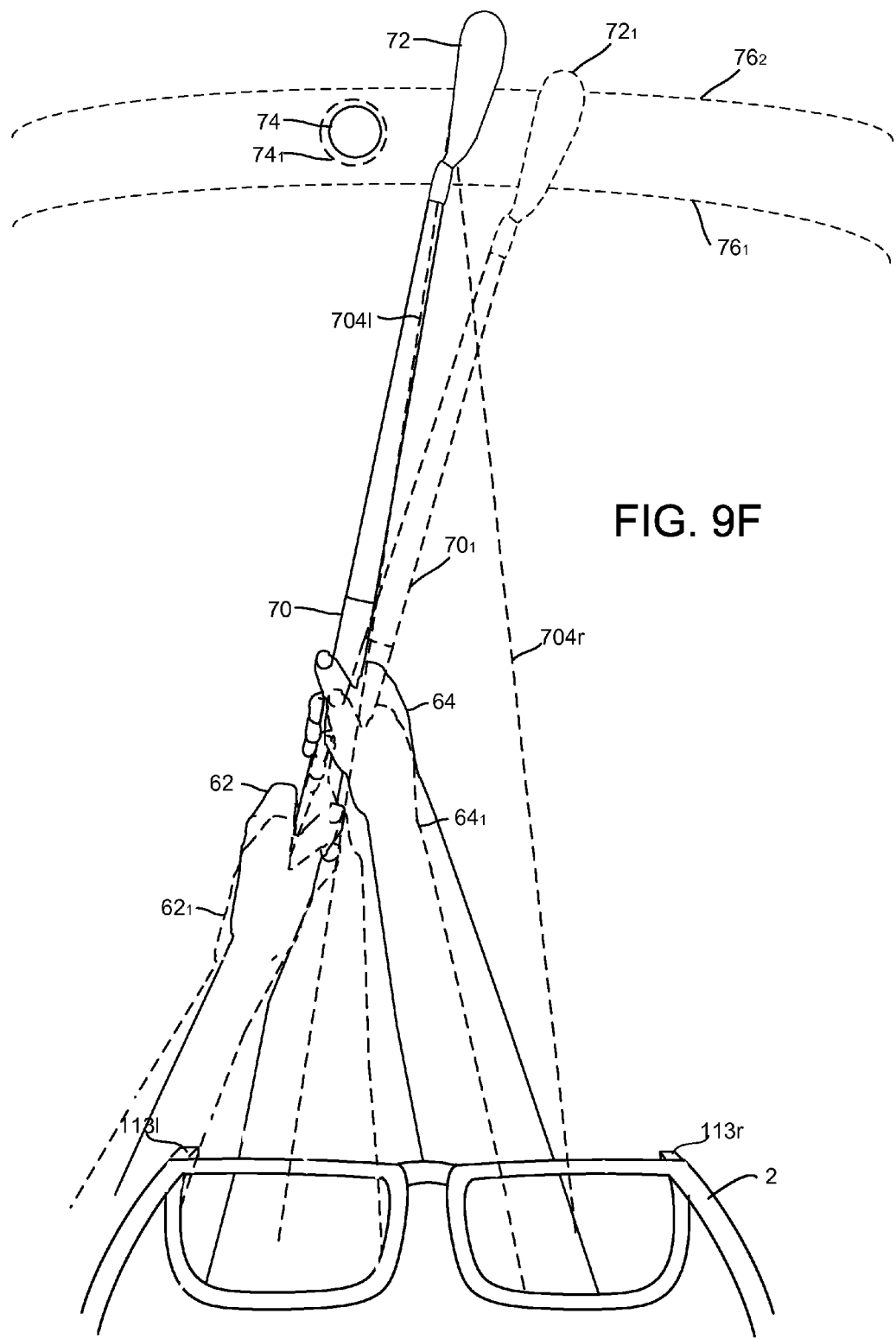
FIG. 9F illustrates another example of visual guides for assisting the user in the example of FIG. 9E see a difference between his performance of the physical movement of a golf swing and a model golf swing for the context.

FIG. 9F illustrates another example of visual guides for assisting the user in the example of FIG. 9E see a difference between his performance of the physical movement of a golf swing and a model golf swing for the context. The visual guides may be displayed while the user is performing his movement or after completing the movement, for example as part of visual feedback, as discussed for FIG. 8A above. If during the movement, 3D virtual data $62_1$ and $64_1$ of the user's hands are displayed along with a virtual version of the club $70_1$ and club head $72_1$ showing a recommended swing in motion toward the ball in the recommended swing path delineated by lines or curves $76_2$ and $76_1$. As illustrated, the user has moved the club too forward in the swing and as contact sensor data will likely show is going to hit the ball 74 too close to the club rather than in a center of the club head 72. As the user's gaze has been on the club head 72 as indicated rather than the ball 74, a visual guide of a highlighted circle $74_1$ is displayed surrounding the ball.

FIG. 9F may also represent visual feedback of a physical movement after completion as discussed in FIG. 8A. Virtual data of the user's actual swing as represented by virtual hands in this example 64, 62, club 70 and club head 72 is displayed. Gaze lines **704*l* and 704*r* may be displayed for the user along with visual highlight $74_1$ on the ball to show him how his eyes were not focused on the ball, but on the club. The reference model for the swing based on the user selection of club seven, which may have been the recommendation of the sport engine 414** or the user's selection in rejection of the recommendation, is also displayed as represented by dashed versions of the user hands $62_1$ and $64_1$, the swing path $76_1$ and $76_2$, the club $70_1$ and the club head $72_1$.

FIG. 9G illustrates an example of displaying virtual data of an avatar interacting with a user during a sport performance session. In this example, Joe is playing virtual basketball with his friend Jim 24 who is playing remotely on a real court. As Joe has released the ball, Jim 24 tries to block the virtual basketball 30 from reaching the basketball hoop 38 while attempting to block Joe from reaching the ball.

Below is described an embodiment of a personal A/V apparatus provide a personalized experience for the user while playing a sport. In one embodiment, a user operating the personal A/V apparatus will be provided with assistance during a game. For example, in golf the personal A/V apparatus can act like a virtual caddy that suggests shots, suggests clubs, advises for weather conditions, provides strategy and automatically tracks the ball after being hit. In one embodiment, the personal A/V apparatus will also display the results of another player (e.g., a friend or famous player) for the same golf course so that the user can play against the other player. This technology can be used for sports other than golf. As described above, some embodiments, a user could actually play with the other player. A hologram of that player could appear on the course and tee up before or after the user. This may be previously captured data that has been uploaded and would then be specific to that course or as in the embodiment of FIG. 3, the sport engine 414 can communicate with the physics engine 308 for coordinating interactive play.

Figure 10:
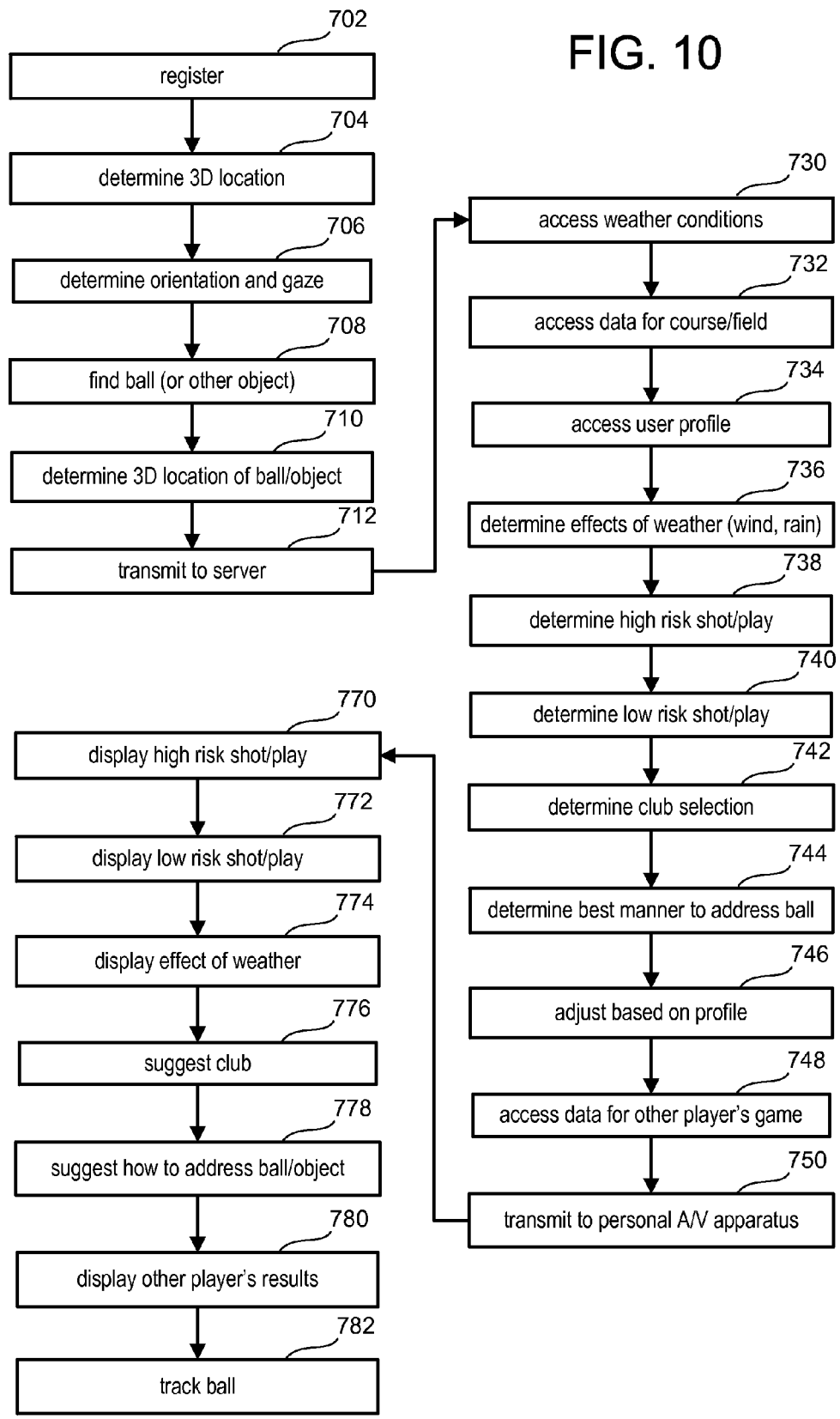
FIG. 10 is a flow chart describing one embodiment of a method for providing a customized experience while a user performs a sport.

FIG. 10 is a flowchart describing one embodiment of a process for providing a personalized experience for a user while the user plays a sport. In this embodiment, the steps on the left side of FIG. 10 are be performed by a personal A/V apparatus 8 while the steps on the right side of the FIG. 10 are performed by a Virtual Data Provider System 404. In step 702, personal A/V apparatus 8 registers (e.g., including authenticate and/or authorize). In step 704, personal A/V apparatus 8 will determine its three dimensional location in real world space. In step 706, personal A/V apparatus 8 will determine its orientation and the gaze of the user. In step 708, personal A/V apparatus 8 will find the ball. In one example, the system is used at a golf course and data from one or more outward facing capture devices 113 can be used to find a golf ball on the course, and can also be used to help aid in finding the location of the personal A/V apparatus 8. Available image and depth data from other capture devices at the course may also be used in tracking the ball and determining location. In step 710, personal A/V apparatus 8 determines the three dimensional location of the ball. Note that this system can be used with games other than golf therefore other sport objects can also be located. In step 712, the information determined in steps 704-710 is transmitted to the Virtual Data Provider System 404. In one embodiment a GPS receiver would be in the ball.

In step 730, Virtual Data Provider System 404 accesses weather conditions, including wind speed, wind direction and precipitation information. In step 732, data is accessed for the golf course (or other type of field). This data will include the map of the field, contours, indications of traps, etc. In step 734, Virtual Data Provider System 404 will access user profile data for the user who registered at step 702 (the information about the identity of the user was provided in step 712). In step 736, Virtual Data Provider System 404 determines the effects of weather (e.g. wind, rain). In step 738, Virtual Data Provider System 404 determines a high risk shot (or other type of play for other sports) based on the location of the personal A/V apparatus 8, the location of the ball, weather conditions and the course information accessed in 732. Using the same data, the system will determine a low risk shot/play in step 740. Virtual Data Provider System 404 determines the appropriate clubs to use for a shot in step 742. The manner for best addressing the ball is determined in step 744, including where to stand and what orientation for the user to put his or her body.

In step 746, the information determined above in steps 736-744 can be adjusted based on the accessed user profile data. For example, if the user is a particularly unskilled player or a novice, the system will choose a recommendation that is easier to accomplish.

In step 748, data for another player's game will also be accessed. For example, the user may want to play against a friend who previously played the same course. Alternatively, the use may want to play against a famous player (such as a professional player) who played the same course. Information for the other player for the same hole (or same shot or same play) will be accessed in step 748. In step 750, the information determined in steps 736-748 is sent back to personal A/V apparatus 8.

In step 770, the high risk shot/play is reported to the user by displaying the information in the personal A/V apparatus 8. In step 772, personal A/V apparatus 8 will display the low risk shot/play. In step 774, effect of weather will be displayed. In step 776, suggestion of which club to use will be displayed to the user. In step 778, a suggestion of how to address the ball will be displayed in the personal A/V apparatus. For example, a diagram of where to stand and how to hit the ball can be displayed in the see-through optical system of the personal A/V apparatus in manner such that the user can see the actual ball unoccluded by any virtual data. In step 780, personal A/V apparatus 8 will display the other player's results. For example, the system can display a video of the other player can be shown, an animation of what happened when the other player played the same course, or text identifying the results for the other player. Note that the information displayed in steps 770-780 will be displayed by the optical system within the personal A/V apparatus (as discussed above). In one embodiment, the system can ghost the user with the user's last time played there.

After step 780, it is assumed that the player will hit the ball. In step 782, the personal A/V apparatus 8 will automatically track the ball so that when the balls lands, the personal A/V apparatus can render an arrow (or other shape) in the display field of view in the personal A/V apparatus to show the user where the ball is. Additionally, user profile data can be updated based on performance of the shot.

Many of the embodiments described herein include storing data about a user, objects and places. This data is then used to augment reality when looking through a personal A/V apparatus. To allow for the efficient storage of such data and exchange of such data, it is contemplated to have a predetermined standard format for storing that data. An example of such a format is referred to as a holographic file format. Use of a holographic file format will allow for portability of data between platforms, compressing the data, use of smart objects, and facilitating virtual representation of real world objects. For more information about some embodiments of a holographic file format, see U.S. patent application Ser. No. 13/430,972, Geisner et al., entitled "Personal Audio/Visual System with Holographic Objects," filed Mar. 27, 2012, which is hereby incorporated herein by reference.

FIG. 11 is a block diagram of one embodiment of a computing system that can be used to implement one or more network accessible computer systems 12 or a companion processing module 4 which may host at least some of the software components of computing environment 54 or other elements depicted in FIG. 3. With reference to FIG. 11, an exemplary system includes a computing device, such as computing device 900. In its most basic configuration, computing device 900 typically includes one or more processing units 902 including one or more central processing units (CPU) and one or more graphics processing units (GPU). Computing device 900 also includes memory 904. Depending on the exact configuration and type of computing device, memory 904 may include volatile memory 905 (such as RAM), non-volatile memory 907 (such as ROM, flash memory, etc.) or some combination of the two. This most basic configuration is illustrated in FIG. 11 by dashed line 906. Additionally, device 900 may also have additional features/functionality. For example, device 900 may also include additional storage (removable and/or non-removable) including, but not limited to, magnetic or optical disks or tape. Such additional storage is illustrated in FIG. 11 by removable storage 908 and non-removable storage 910.

Device 900 may also contain communications connection(s) 912 such as one or more network interfaces and transceivers that allow the device to communicate with other devices. Device 900 may also have input device(s) 914 such as keyboard, mouse, pen, voice input device, touch input device, etc. Output device(s) 916 such as a display, speakers, printer, etc. may also be included. These devices are well known in the art so they are not discussed at length here.

The example computer systems illustrated in the figures include examples of computer readable storage devices. A computer readable storage device is also a processor readable storage device. Such devices may include volatile and non-volatile, removable and non-removable memory devices implemented in any method or technology for storage of information such as computer readable instructions, data structures, program modules or other data. Some examples of processor or computer readable storage devices are RAM, ROM, EEPROM, cache, flash memory or other memory technology, CD-ROM, digital versatile disks (DVD) or other optical disk storage, memory sticks or cards, magnetic cassettes, magnetic tape, a media drive, a hard disk, magnetic disk storage or other magnetic storage devices, or any other device which can be used to store the information and which can be accessed by a computer.

Although the subject matter has been described in language specific to structural features and/or methodological acts, it is to be understood that the subject matter defined in the appended claims is not necessarily limited to the specific features or acts described above. The specific features and acts described above are disclosed as example forms of implementing the claims.

What is claimed is:

1. A method for providing a personalized sport performance experience with three dimensional (3D) virtual data being displayed by a near-eye, augmented reality (AR) display of a personal audiovisual (A/V) apparatus comprising:
   identifying a physical location which the personal A/V apparatus is within based on location data detected by the personal A/V apparatus;
   identifying one or more 3D space positions of at least one or more sport objects in a sport performance area associated with the physical location based on a three dimensional mapping of objects in the sport performance area;
   accessing a memory for physical characteristics including one or more physical dimensions of a user and skills data for a sport stored for the user in user profile data;
   determining a physical movement recommendation by a processor for the user performing the sport based on the skills data for the sport, the physical characteristics including one or more physical dimensions of the user, and 3D space positions for at least the one or more sport objects; and
   displaying three-dimensional (3D) virtual data depicting one or more visual guides from a displaying three-dimensional (3D) virtual data depicting one or more visual guides from a user perspective in a display field of view of the near-eye AR display, the one or more visual guides including image data of one or more of the user's body parts of execution of the physical movement recommendation displayed from the perspective of the user during execution of the physical movement recommendation by the user and which displayed visual guides can be followed by one or more actual body parts of the user by placement over the visual guides in the display field of view during the execution of the physical movement recommendation.

2. The method of claim 1 wherein the one or more visual guides include image data of one or more body parts moving in relation to a sport object for the sport from the user perspective associated with the display field of view.

3. The method of claim 2 wherein the physical characteristics of the user include physical dimensions of the user and a strength rating.

4. The method of claim 1 further comprising:
   tracking an actual physical movement of the user in performing the sport based on image and depth data from one or more capture devices in the physical location.

5. The method of claim 4 further comprising:
   tracking motion of a real sport object set in motion by the actual physical movement of the user based on sensor data; and
   displaying virtual data illustrating the motion of the real sport object.

6. The method of claim 4 further comprising:
   displaying 3D virtual data illustrating motion of a virtual sport object responsive to the actual physical movement of the user from the user perspective associated with the display field of view.

7. The method of claim 1 further comprising:
   determining the physical movement recommendation by the processor for the user performing the sport based on environmental conditions in the sport performance area.

8. The method of claim 1 wherein the one or more sport objects include a virtual object and a real object.

9. The method of claim 1 further comprising:
   displaying a virtual sport performance area for the user performing the sport; and
   determining the physical movement recommendation by the processor for the user based on one or more features in the virtual sport performance area.

10. The method of claim 1 wherein the one or more visual guides including image data of a reference model of execution of the physical movement recommendation comprises image data of one or more body parts used during execution of the physical movement recommendation.

11. The method of claim 1 wherein the one or more visual guides including image data of a reference model of execution of the physical movement recommendation comprises image data of one or more of the user's own body parts which the user can place his or her one or more actual body parts over and follow during execution of the physical movement recommendation.

12. A portable personal audiovisual (A/V) apparatus for providing a personalized sport performance experience with three dimensional (3D) virtual data comprising:
   a near-eye, augmented reality display having a display field of view and being supported by a near-eye support structure;
   one or more processors having access to memory storing physical characteristics including one or more physical dimensions of a user wearing the personal A/V apparatus and skills data for the user for one or more sports;
   a natural user interface including at least one image capture device communicatively coupled to the one or more processors and being supported by the near-eye support structure for tracking a physical sport movement being performed by a user;
   the one or more processors executing software for determining a physical sport movement recommendation having a sport objective score for each physical sport movement based on a probability of success in achieving at least one sport objective performed by the user based on a sport being performed and weighted based on a current context of a session of the performance, the physical characteristics including one or more physical dimensions of the user wearing the personal A/V apparatus, skills data for the user for the sport being played and one or more objects in a sport performance area in which the user is performing the sport; and
   the one or more processors controlling the near-eye, augmented reality display of the personal A/V apparatus for displaying three-dimensional (3D) virtual data depicting one or more visual guides from a user perspective in the display field of view of the near-eye AR display, the one or more visual guides including image data of a reference model of execution of the physical sport movement recommendation displayed from the perspective of the user during execution of the physical sport movement recommendation by the user and which displayed visual guides can be followed by one or more actual body parts of the user in the display field of view during the execution of the physical movement recommendation.

13. The apparatus of claim 12 further comprising:
a location sensing unit for determining a physical location of the user based on non-image sensor data.

14. The apparatus of claim 12 further comprising:
the one or more processors executing software for storing sport performance data representing the physical sport movement in user profile data;
the one or more processors executing software for analyzing the sport performance data in accordance with execution criteria for the tracked physical sport movement and environmental conditions of the sport performance area;
assigning a skill level for the physical sport movement based on execution criteria; and
the one or more processors updating skills data for the sport for the user in the memory based on the assigned skill level for the physical sport movement.

15. The apparatus of claim 14 further comprising:
a microphone of the personal A/V apparatus for capturing a sound made in a physical location by a real sport object,
the one or more processors being communicatively coupled to receive audio data representing the sound from the microphone and executing a sound recognition engine for identifying the sound as a sound related to the physical sport movement; and
the one or more processors comparing the sound related to the physical movement against execution sound criteria for assigning a sound factor; and
the one or more processors assigning the skill level for the physical sport movement based on execution criteria which includes the sound factor.

16. The apparatus of claim 14 further comprising:
the one or more processors determining audio parameters for a contact sound for a virtual sport object contacted in the physical sport movement based on the sports performance data for the physical sport movement;
an audio engine for generating the contact sound related to the physical sport movement in accordance with the audio parameters determined for the contact sound;
the one or more processors executing the audio engine for playing the contact sound with the determined audio parameters through at least one audio output device of the personal A/V apparatus.

17. The apparatus of claim 12 wherein the one or more visual guides including image data of a reference model of execution of the physical movement recommendation comprises image data of one or more body parts used during execution of the physical movement recommendation.

18. The apparatus of claim 12, wherein
a sport objective score is assigned for each physical sport movement of the user based on a probability of success in achieving the at least one sport objective,
a user execution score is assigned for each physical sport movement performed by the user based on the skills data, and
the physical sport movement recommendation score for each physical movement performed by the user is based on a respective sport objective score and user execution score.

19. One or more processor readable storage devices comprising instructions which cause one or more processors to execute a method for providing a personalized sport performance experience with three dimensional (3D) virtual data being displayed by a near-eye, augmented reality (AR) display of a personal audiovisual (A/V) apparatus comprising:
identifying a physical location which the personal A/V apparatus is within based on location data detected by the personal A/V apparatus;
identifying one or more 3D space positions of at least one or more sport objects in a sport performance area associated with the physical location based on a three dimensional mapping of objects in the sport performance area;
accessing a memory for physical characteristics of a user and skills data for a sport stored for the user in user profile data;
determining a physical movement recommendation having a physical sport movement recommendation score satisfying a selection criteria based on a highest combined score for a sport objective score and a user execution score by a processor for the user performing the sport based on the skills data for the sport, the physical characteristics including one or more physical dimensions of the user, and 3D space positions for at least the one or more sport objects; and
displaying three-dimensional (3D) virtual data depicting one or more visual guides from a user perspective in a display field of view of the near-eye AR display, the one or more visual guides including image data of one or more of the user's body parts of execution of the physical movement recommendation displayed from the perspective of the user during execution of the physical movement recommendation by the user and which displayed visual guides can be followed by one or more actual body parts of the user by placement over the visual guides in the display field of view during the execution of the physical movement recommendation.

20. The one or more processor readable storage devices of claim 19 wherein the one or more visual guides including image data of a reference model of execution of the physical movement recommendation comprises image data of one or more body parts used during execution of the physical movement recommendation.

* * * * *